(12) United States Patent
Schroeder et al.

(10) Patent No.: US 12,144,950 B2
(45) Date of Patent: Nov. 19, 2024

(54) CONTAINER FEATURES FOR SURGICAL INSTRUMENT LUBRICANT

(71) Applicant: Cilag GmbH International, Zug (CH)

(72) Inventors: Mallory E. Schroeder, Cincinnati, OH (US); Justin M. Kovach, Cincinnati, OH (US); Sean P. Conlon, Loveland, OH (US); Mark E. Tebbe, Lebanon, OH (US); Louis P. Mingione, Madison, WI (US); Sudha Vijaykumar, Terre Haute, IN (US); Monica L. Rivard, Cincinnati, OH (US); Shane R. Adams, Lebanon, OH (US); Karen M. Averbeck, Dayton, OH (US); Ryan J. Reese, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 153 days.

(21) Appl. No.: 17/721,434

(22) Filed: Apr. 15, 2022

(65) Prior Publication Data
US 2023/0329420 A1 Oct. 19, 2023

(51) Int. Cl.
| A61M 35/00 | (2006.01) |
| A46B 11/00 | (2006.01) |
| A47L 17/10 | (2006.01) |
| B05C 3/02  | (2006.01) |

(52) U.S. Cl.
CPC ....... *A61M 35/006* (2013.01); *A46B 11/0041* (2013.01); *A47L 17/10* (2013.01); *B05C 3/02* (2013.01)

(58) Field of Classification Search
CPC ........... A46B 11/0041; A61M 11/0041; A61M 35/003; B05C 3/02; B05C 3/20; B05C 9/02; B05C 9/04; A47L 21/04; A47L 21/00; A47L 17/00; A47L 13/17; A47L 13/16; A47L 17/10
USPC ....... 401/6, 9, 123, 126, 127, 130; 15/244.1, 15/218.1, 104.92, 236.09
See application file for complete search history.

(56) References Cited

U.S. PATENT DOCUMENTS

| 4,964,372 | A  | * | 10/1990 | Zeenni   | A45D 29/007 |
|           |    |   |         |          | 401/206     |
| 6,500,176 | B1 |   | 12/2002 | Truckai et al. | |
| 6,783,524 | B2 |   | 8/2004  | Anderson et al. | |
| 7,225,814 | B2 | * | 6/2007  | Barclay  | A45D 34/046 |
|           |    |   |         |          | 401/122     |
| 8,888,809 | B2 |   | 11/2014 | Davison et al. | |
| 8,939,974 | B2 |   | 1/2015  | Boudreaux et al. | |
| 8,986,302 | B2 |   | 3/2015  | Aldridge et al. | |
| 9,161,803 | B2 |   | 10/2015 | Yates et al. | |
| 9,526,565 | B2 |   | 12/2016 | Strobl   | |

(Continued)

*Primary Examiner* — David J Walczak
(74) *Attorney, Agent, or Firm* — Frost Brown Todd LLP

(57) ABSTRACT

An apparatus includes an external body, a floor attached to the external body, an applicator pad, and a cover. The external body defines an internal cavity and extends between a bottom and top end. The applicator pad extends from the floor into the internal cavity defined by the external body. The applicator pad has an absorbent material that can absorb an electro-lubricant. The applicator pad is dimensioned to be grasped by a pair of jaws of a surgical instrument. The cover is associated with the top end of the external body and partially defines the internal cavity of the external body. The cover allows the pair of jaws to enter the internal cavity via the cover to grasp the applicator pad.

17 Claims, 19 Drawing Sheets

(56) References Cited

U.S. PATENT DOCUMENTS

| | | |
|---|---|---|
| 9,545,253 B2 | 1/2017 | Worrell et al. |
| 9,877,720 B2 | 1/2018 | Worrell et al. |
| 11,097,027 B2 * | 8/2021 | Erwin .................. B43K 23/002 |
| 2006/0042655 A1 * | 3/2006 | Beatty ...................... B08B 1/00 15/210.1 |
| 2023/0329742 A1 | 10/2023 | Boronyak et al. |

* cited by examiner

CONTAINER FEATURES FOR SURGICAL INSTRUMENT LUBRICANT

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein, in its entirety; U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein, in its entirety; U.S. Pat. No. 8,888,809, entitled "Surgical Instrument with Jaw Member," issued Nov. 18, 2014, the disclosure of which is incorporated by reference herein, in its entirety; U.S. Pat. No. 9,161,803, entitled "Motor Driven Electrosurgical Device with Mechanical and Electrical Feedback," issued Oct. 20, 2015, the disclosure of which is incorporated by reference herein, in its entirety; U.S. Pat. No. 9,877,720, entitled "Control Features for Articulating Surgical Device," issued Jan. 30, 2018, the disclosure of which is incorporated by reference herein, in its entirety; U.S. Pat. No. 9,545,253, entitled "Surgical Instrument with Contained Dual Helix Actuator Assembly," issued Jan. 17, 2017, the disclosure of which is incorporated by reference herein, in its entirety; and U.S. Pat. No. 9,526,565, entitled "Electrosurgical Devices," issued Dec. 27, 2016, the disclosure of which is incorporated by reference herein, in its entirety.

While a variety of surgical instruments and accessories have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
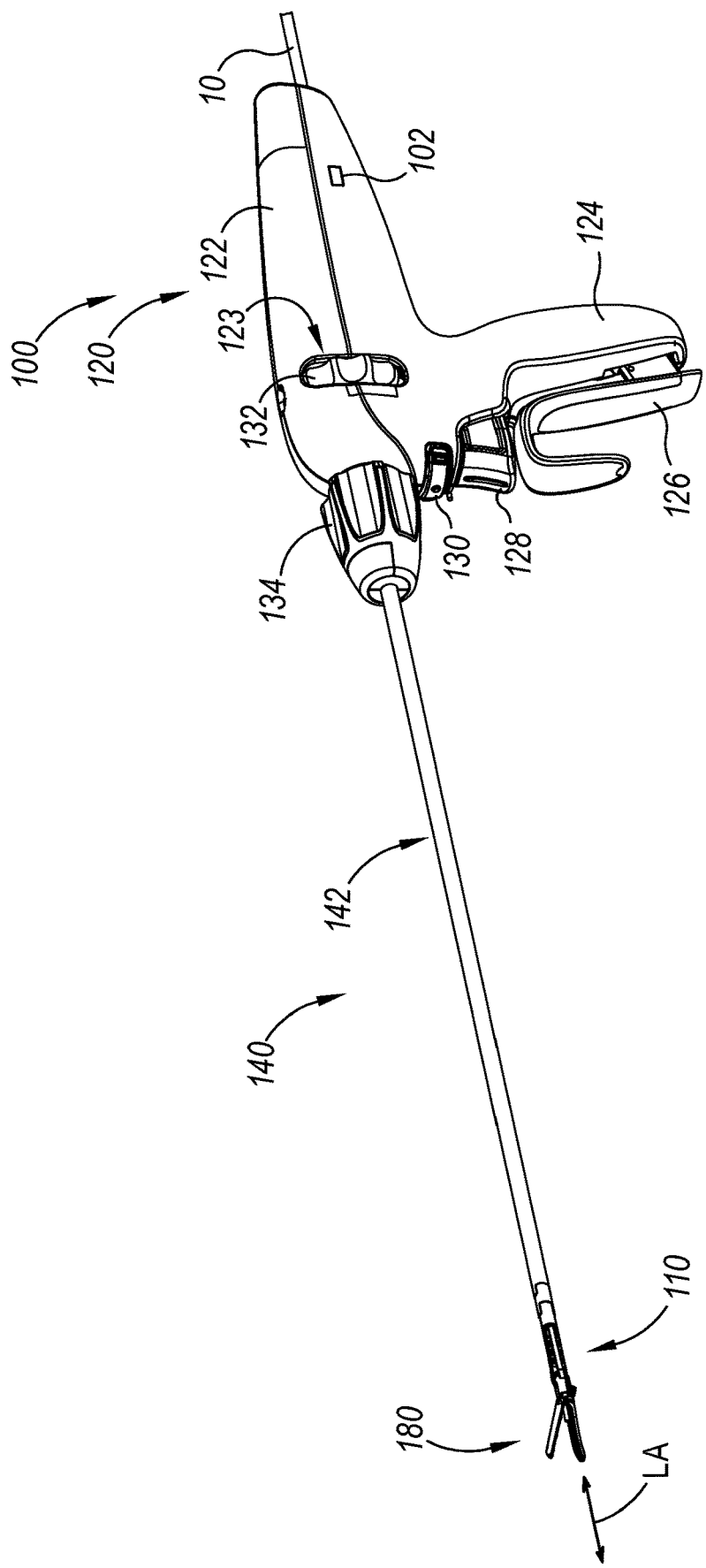
FIG. 1 depicts a perspective view of an exemplary electrosurgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Example of Electrosurgical Instrument

Figure 2:
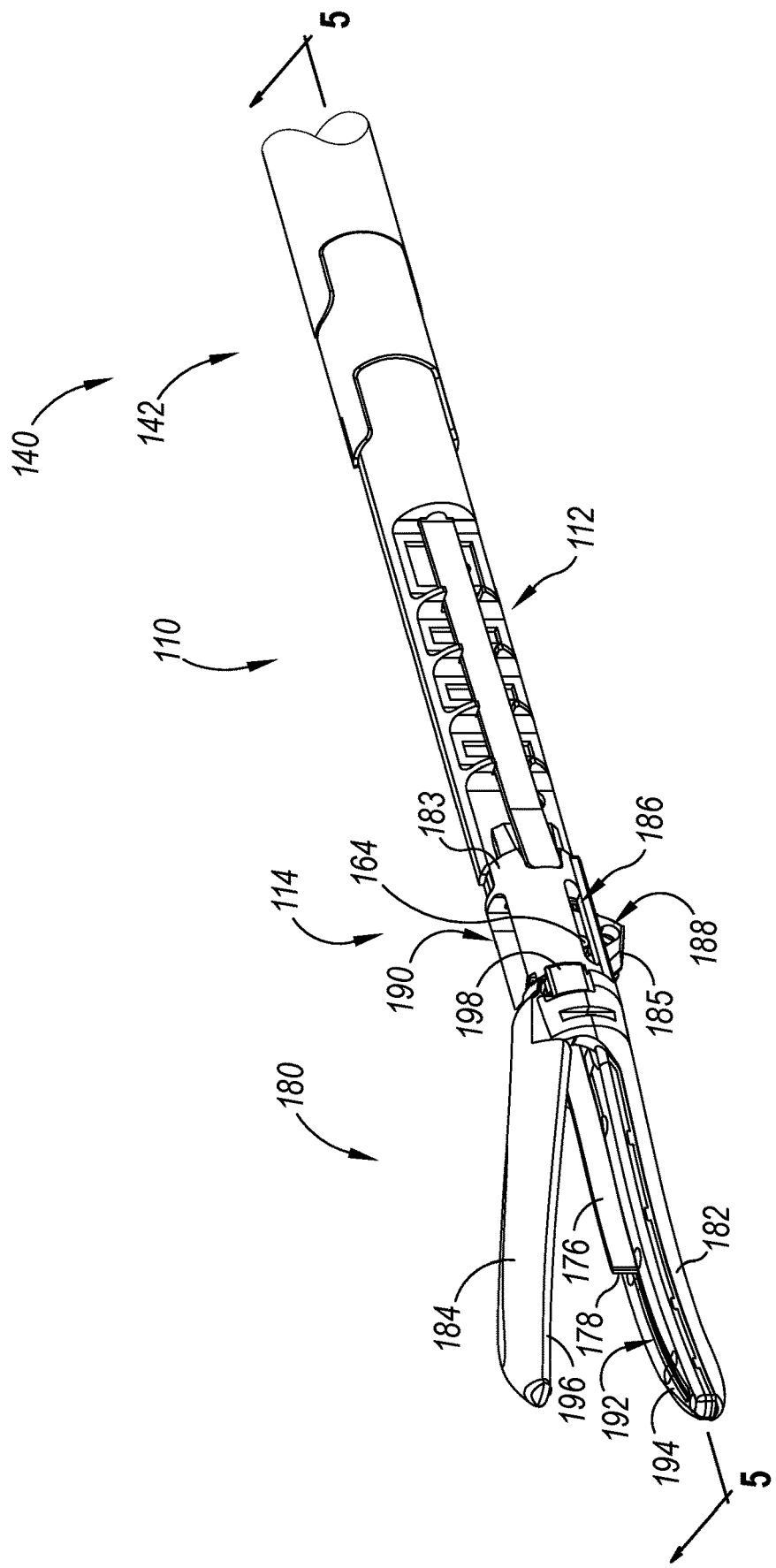
FIG. 2 depicts a perspective view of an exemplary articulation assembly and end effector of the electrosurgical instrument of FIG. 1.

FIGS. 1-2 show an exemplary electrosurgical instrument (100). As best seen in FIG. 1, electrosurgical instrument (100) includes a handle assembly (120), a shaft assembly (140), an articulation assembly (110), and an end effector (180). As will be described in greater detail below, end effector (180) of electrosurgical instrument (100) is operable to grasp, cut, and seal or weld tissue (e.g., a blood vessel, etc.). In this example, end effector (180) is configured to seal or weld tissue by applying bipolar radio frequency (RF) energy to tissue. However, it should be understood electrosurgical instrument (100) may be configured to seal or weld tissue through any other suitable means that would be apparent to one skilled in the art in view of the teachings herein. For example, electrosurgical instrument (100) may be configured to seal or weld tissue via an ultrasonic blade, staples, etc. In the present example, electrosurgical instrument (100) is electrically coupled to a power source (not shown) via power cable (10).

The power source may be configured to provide all or some of the electrical power requirements for use of electrosurgical instrument (100). Any suitable power source may be used as would be apparent to one skilled in the art in view of the teachings herein. By way of example only, the power source may comprise a GEN04 or GEN11 sold by Ethicon Endo-Surgery, Inc. of Cincinnati, Ohio. In addition, or in the alternative, the power source may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein, in its entirety. While in the current example, electrosurgical instrument (100) is coupled to a power source via power cable (10), electrosurgical instrument (100) may contain an internal power source or plurality of power sources, such as a battery and/or supercapacitors, to electrically power electrosurgical instrument (100). Of course, any suitable combination of power sources may be utilized to power electrosurgical instrument (100) as would be apparent to one skilled in the art in view of the teaching herein.

Handle assembly (120) is configured to be grasped by an operator with one hand, such that an operator may control and manipulate electrosurgical instrument (100) with a single hand. Shaft assembly (140) extends distally from handle assembly (120) and connects to articulation assembly (110). Articulation assembly (110) is also connected to a proximal end of end effector (180). As will be described in greater detail below, components of handle assembly (120) are configured to control end effector (180) such that an operator may grasp, cut, and seal or weld tissue. Articulation assembly (110) is configured to deflect end effector (180) from the longitudinal axis (LA) defined by shaft assembly (140).

Handle assembly (120) includes a control unit (102) housed within a body (122), a pistol grip (124), a jaw closure trigger (126), a knife trigger (128), an activation button (130), an articulation control (132), and a knob (134). As will be described in greater detail below, jaw closure trigger (126) may be pivoted toward and away from pistol grip (124) and/or body (122) to open and close jaws (182, 184) of end effector (180) to grasp tissue. Additionally, knife trigger (128) may be pivoted toward and away from pistol grip (124) and/or body (122) to actuate a knife member (176) within the confines of jaws (182, 184) to cut tissue captured between jaws (182, 184). Further, activation button (130) may be pressed to apply radio frequency (RF) energy to tissue via electrode surfaces (194, 196) of jaws (182, 184), respectively.

Body (122) of handle assembly (120) defines an opening (123) in which a portion of articulation control (132) protrudes from. Articulation control (132) is rotatably disposed within body (122) such that an operator may rotate the portion of articulation control (132) protruding from opening (123) to rotate the portion of articulation control (132) located within body (122). Rotation of articulation control (132) relative to body (122) is configured to bend articulation section (110) in order to drive deflection of end effector (180) from the longitudinal axis (LA) defined by shaft assembly (140). Articulation control (132) and articulation section (110) may include any suitable features to drive deflection of end effector (180) from the longitudinal axis (LA) defined by shaft assembly (140) as would be apparent to one skilled in the art in view of the teachings herein.

Knob (134) is rotatably disposed on the distal end of body (122) and configured to rotate end effector (180), articulation assembly (110), and shaft assembly (140) about the longitudinal axis (LA) of shaft assembly (140) relative to handle assembly (120). While in the current example, end effector (180), articulation assembly (110), and shaft assembly (140) are rotated by knob (134), knob (134) may be configured to rotate end effector (180) and articulation assembly (110) relative to selected portions of shaft assembly (140). Knob (134) may include any suitable features to rotate end effector (180), articulation assembly (110), and shaft assembly (140) as would be apparent to one skilled in the art in view of the teachings herein.

Shaft assembly (140) includes distal portion (142) extending distally from handle assembly (120), and a proximal portion housed within the confines of body (122) of handle assembly (120). Shaft assembly (140) houses a jaw closure connector that couples jaw closure trigger (126) with end effector (180). Additionally, shaft assembly (140) houses a portion of knife member extending between distal cutting edge (178) and knife trigger (128). Shaft assembly (140) also houses actuating members (112) that couple articulation assembly (110) with articulation control (132); as well as an electrical connecter that operatively couples electrode surfaces (194, 196) with activation button (130). As will be described in greater detail below, jaw closure connector is configured to translate relative to shaft assembly (140) to open and close jaws (182, 184) of end effector (180); while knife member (176) is coupled to knife trigger (128) of handle assembly (120) to translate distal cutting edge (178) within the confines of end effector (180); and activation button (130) is configured to activate electrode surface (194, 196).

As best seen in FIGS. 2, end effector (180) includes lower jaw (182) pivotally coupled with upper jaw (184) via pivot couplings (198). Lower jaw (182) includes a proximal body (183) defining a slot (186), while upper jaw (184) includes proximal arms (185) defining a slot (188). Lower jaw (182) also defines a central channel (190) that is configured to receive proximal arms (185) of upper jaw (184), portions of knife member (176), jaw closure connecter, and pin (164). Slots (186, 188) each slidably receive pin (164), which is attached to jaw closure connector.

Jaw closure trigger (126) is operatively connected with pin (164) such that pivoting of jaw closure trigger (126) relative to pistol grip (124) drives translation of pin (164). Since pin (164) is located within both slots (186, 188), and slots (186, 188) are angled relative to each other, translation of pin (164) cams against proximal arms (185) to pivot upper jaw (184) toward and away from lower jaw (182) about pivot couplings (198). Therefore, upper jaw (184) is configured to pivot toward and away from lower jaw (182) about pivot couplings (198) to grasp tissue in response to pivoting jaw closure trigger (126) relative to pistol grip (124). Jaw closure trigger (126) may be biased to a position such that jaws (182, 184) are in an open configuration.

Lower jaw (182) and upper jaw (184) also define a knife pathway (192). Knife pathway (192) is configured to slidably receive knife member (176), such that knife member (176) may be retracted and advanced to cut tissue captured between jaws (182, 184). As mentioned above, knife trigger (128) is operatively coupled with knife member (176) such that actuation of knife trigger (128) toward and away from pistol grip (124) and/or body (122) actuates knife member (176) within the confines of jaws (182, 184). Knife trigger (128) may be biased to a position such that knife member (176) is in a proximal, pre-fired, position.

Lower jaw (182) and upper jaw (184) each comprise a respective electrode surface (194, 196). The power source may provide RF energy to electrode surfaces (194, 196) via electrical coupling that extends through handle assembly (120), shaft assembly (140), articulation assembly (110), and electrically couples with one or both of electrode surfaces (194, 196). Electrical coupling may selectively activate electrode surfaces (194, 196) in response to an operator pressing activation button (130). In some instances, control unit (102) may couple electrical coupling with activation button (130), such that control unit (102) activates electrode surfaces (194, 196) in response to operator pressing activation button (130). Control unit (102) may have any suitable components in order to perform suitable functions as would be apparent to one skilled in the art in view of the teachings herein. For instance, control unit (102) may have a processor, memory unit, suitable circuitry, etc.

During exemplary use, jaw closure trigger (126) may be pivoted toward and away from pistol grip (124) and/or body (122) to open and close jaws (182, 184) of end effector (180) to grasp tissue. In particular, pivoting jaw closure trigger (126) toward pistol grip (124) may proximally actuate pin (164), which in turn cams against slots (188) of proximal arms (185) of upper jaw (184), thereby rotating upper jaw (184) about pivot couplings (198) toward lower jaw (182) such that jaws (182, 184) achieve a closed configuration.

Subsequently, after suitably grasping tissue in accordance with the description herein, knife trigger (128) may be actuated toward and away from body (122) and/or pistol grip (124) to actuate knife member (176) within knife pathway (192) of jaws (182, 184) to cut tissue captured between jaws (182, 184).

Before or after firing of knife member (176) in accordance with the description herein, an operator may press activation button (130) to selectively activate electrode surfaces (194, 196) of jaws (182, 184) with RF energy to weld/seal tissue that is captured between jaws (182, 184). It should be understood that the operator may also press activation button (130) to selectively activate electrode surfaces (194, 196) of jaws (182, 184) at any suitable time during exemplary use. Next, the operator may release jaw closure trigger (126) such that jaws (182, 184) pivot into the opened configuration, releasing tissue.

In some instances, electrode surfaces (194, 196) may be configured to apply a suitable amount of RF energy to tissue in order to cut tissue grasped by jaws (182, 184). Further, in some instances knife member (74) may be omitted entirely,

II. Exemplary Container Features for Surgical Instrument Lubricant

As mentioned above, end effector (180) includes a pair of electrodes surfaces (194, 196) associated with a respective jaw (182, 184) that are configured to grasp tissue. As also mentioned above, electrode surfaces (194, 196) are configured to apply RF energy to grasped tissue in order to suitably weld/seal the grasped tissue. During exemplary use of end effector (180), tissue may undesirably tend to stick to jaws (182, 184) of end effector (180) during exemplary use in accordance with the description herein. For example, the compressive forces of closing jaws (182, 184) onto tissue and/or thermal energy generated from activated electrode surfaces (194, 196) may undesirably promote sticking between end effector (180) and tissue. Additionally, dead tissue (e.g., eschar) may tend to accumulate on end effector (180) in response to such exemplary use in accordance with the description herein.

In order to inhibit such undesirable consequences during exemplary use of end effector (180), an electro-lubricant may be applied to surfaces of end effector (180) intended to directly contact tissue during exemplary use (e.g., electrode surfaces (194, 196)). Electro-lubricants may be a viscous, anti-stick, non-toxic, biocompatible phospholipid solution that is applied to end effector (180) prior to exemplary use. Electro-lubricants may include any suitable materials as would be apparent to one skilled in the art in view of the teachings herein.

Application of electro-lubricant may be performed prior to a surgical procedure. It may be desirable to apply an even coating of electro-lubricant to tissue engaging surfaces of end effector (180). In some instances, one application of electro-lubricant is enough to complete a desired surgical procedure such that surfaces of end effector (180) do not undesirably stick to tissue. However, the effectiveness of electro-lubricants may tend to deteriorate over time in response to numerous activations of electrode surfaces (194, 196). Additionally, an excess amount of eschar may tend to accumulate on electrode surfaces (194, 196) after numerous activations in accordance with the description herein. In instances where electrode surfaces (194, 196) are activated numerous times, it may be desirable to reapply electro-lubricant to jaws (182, 184) of an end effector (180) during a surgical procedure and/or remove accumulated eschar from electrode surfaces (194, 196). In instances where electro-lubricant is reapplied to end effector (180), an excess amount of electro-lubricant may be accidentally applied to the surfaces of end effector (180), such that it may be desirable to remove excess electro-lubricant from end effector (180) while also applying an even layer of electro-lubricant to end effector (180). Therefore, it may be desirable to reapply electro-lubricant to jaws (182, 184) in a reliable and effective manner such that an even coating of electro-lubricant is easily and efficiently applied to desired surfaces of end effector (180).

Figure 3:
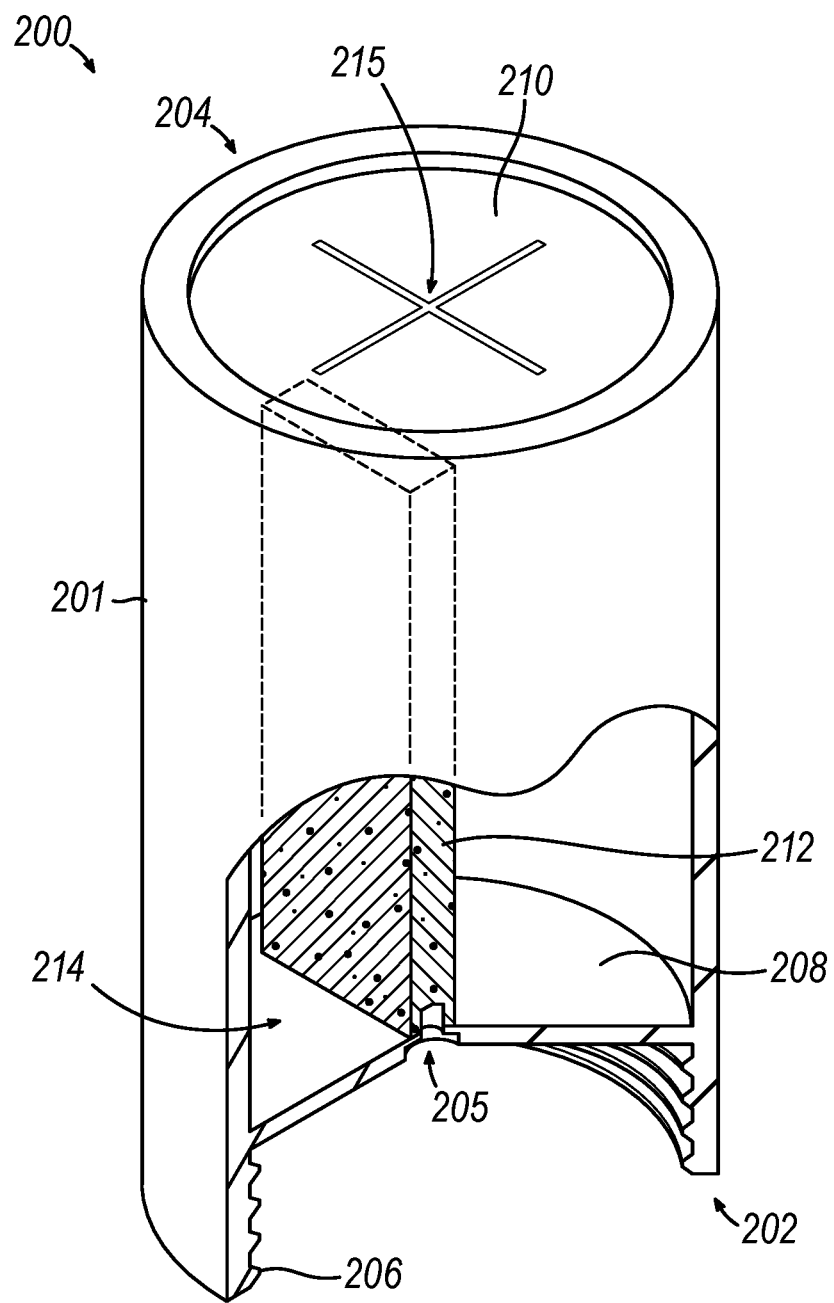
FIG. 3 depicts a partial sectional perspective view of an exemplary electro-lubricant applicator.

FIG. 3 depicts an exemplary electro-lubricant applicator (200) that may be utilized in accordance with the description herein in order to apply an even coating of electro-lubrication to desired surfaces of end effector (180) in a reliable, effective, easy, and efficient manner. Applicator (200) includes a cap body (201) that extends between a bottom portion (202) and a top portion (204).

Bottom portion (202) of cap body (201) includes a fluid source coupling feature, which is a threaded portion (206) in the current aspect of the disclosure. Additionally, bottom portion (202) includes a floor (208) which partially defines an internal chamber (214) housing an absorbent applicator pad (212). Absorbent applicator pad (212) is attached to floor (208) and extends upwardly from floor (208) toward top portion (204) of applicator (200). Floor (208) defines a fluid pathway (205) that extends from a bottom surface of floor (208) through a top surface of floor (208) that is in fluid communication with absorbent applicator pad (212).

Absorbent applicator pad (212) is formed of a suitable material such that absorbent applicator pad (212) may absorb an electro-lubricant (L) and maintain its intended shape such that end effector (180) may grasp pad (212). Additionally, pad (212) is formed of a suitable material such that pad (212) may transfer absorbed electro-lubricant to jaws (182, 184) in response to end effector (180) grasping pad (212) with a suitable compressive force. In the current aspect of the disclosure, absorbent applicator pad (212) is dimensioned to suitably engage electrode surface (194, 196) in response to end effector (180) grasping pad (212). Therefore, pad (212) is large enough such that desired portions of electrode surfaces (194, 196) are in direct contact with pad (212) while end effector (180) grasps pad (212). It should be understood that pad (212) may have any suitable dimensions/geometry as would be apparent to one skilled in the art in view of the teachings herein. As will be described in greater detail below, absorbent applicator pad (212) is configured to absorb a suitable amount of electro-lubricant (L) while maintaining its shape such that jaws (182, 184) of end effector (180) may grasp pad (212) in order to a apply electro-lubricant (L) to electrode surfaces (194, 196).

Female threaded portion (206) is configured to selectively couple applicator (200) onto an open end of an electro-lubricant container (C) filled with electro-lubricant (L). In particular, female threaded coupling portion (206) is configured to mesh with a male threading of container (C) located at an open end of container (C) in order to selectively attach applicator (200) with container (C). While threads are used in the current example, applicator (200) may selectively couple with container (C) using any suitable means as would be apparent to one skilled in the art in view of the teachings herein. For example, Applicator (200) may couple to container (C) via a snap-fitting, an interference fit, use of elastomeric O-rings, etc.

While applicator (200) is attached to container (C), fluid pathway (205) of floor (208) is in fluid communication with electro-lubricant (L) housed within container (C). Since fluid pathway (205) is in fluid communication with absorbent pad (212), fluid pathway (205) provides fluid communication between the interior of container (C) and absorbent pad (212) while applicator (200) is attached to container (C). Therefore, while applicator (200) is attached to container (C), electro-lubricant (L) may travel between the interior of container (C) and absorbent pad (212) via pathway (205).

Top portion includes a top cover, currently in the form of an elastomeric seal (210) defining an expandable opening (215). Elastomeric seal (210) is located above pad (212) such that seal (210) partially defines internal chamber (214) housing pad (212).

Expandable opening (215) of seal (210) is naturally in a closed configuration and further configured to expand into an open configuration in response to end effector (180) being inserted into chamber (214). In the closed configuration, elastomeric seal (210) may prevent unwanted fluid/materials from entering internal chamber (214). Additionally, while in the closed configuration, elastomeric seal (210) may prevent any accumulated electro-lubricant (L) within chamber (214) from accidentally exiting chamber (214) via top portion (204). In the open configuration, expandable opening (215) of seal (210) is configured to expand to thereby accommodate the insertion of end effector (180) into chamber of applicator (200) in accordance with the description herein. Seal (210) is resiliently biased toward the closed configuration. Therefore, in the expanded state, seal (210) is sufficiently resilient to conform to the outer surface of end effector (180) to inhibit transfer the fluid/minerals into and out of chamber (214), in a similar fashion to when seal (210) is in the closed configuration.

Seal (210) may be formed of any suitable material as would be apparent to one skilled in the art in view of the teachings herein. Additionally, seal (210) may include any suitable structures as would be apparent to one skilled in the art in view of the teachings herein. For example, seal (210) may take the form of a duckbill seal. In some instances, seal (210) merely acts as a cover and does not function as a traditional seal. In some instances, seal (210) may be entirely omitted.

Figure 4A:
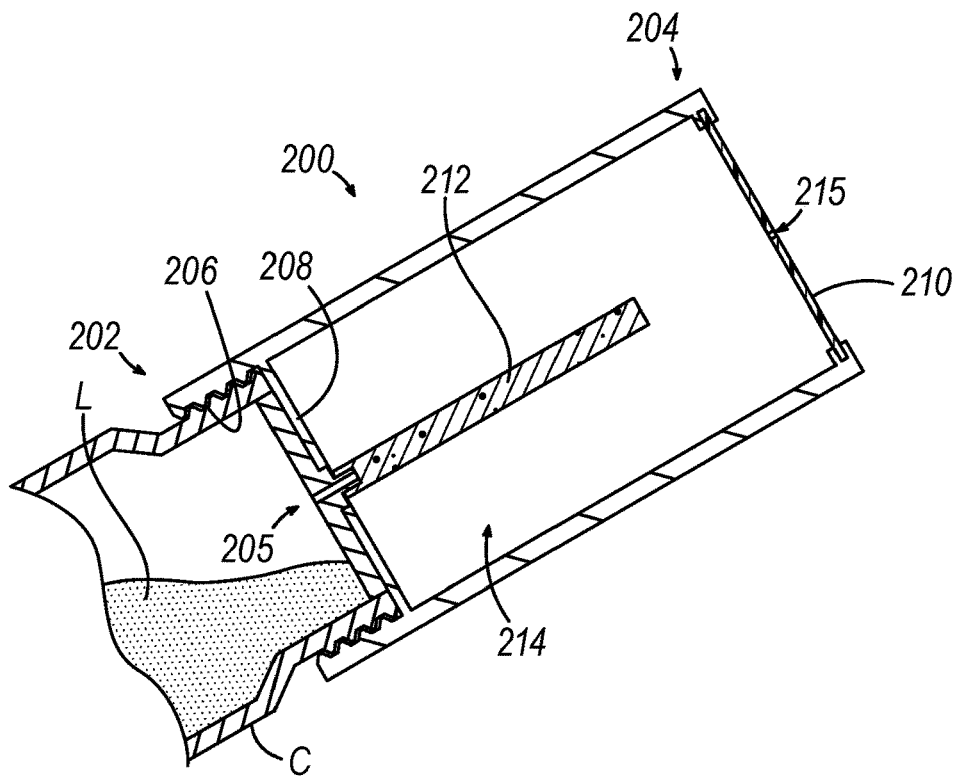
FIG. 4A depicts a cross-sectional view of the electro-lubricant applicator of FIG. 3, taken along a centerline thereof, coupled to a source of electro-lubricant in an upwardly tilted position.

FIGS. 4A-4F show an exemplary use of applicator (200) in order to apply an even coating of electro-lubrication to desired surfaces of end effector (180) in a reliable, effective, easy, and efficient manner. First, a user may attach applicator (200) to container (C) as shown in FIG. 4A such that electro-lubricant (L) within container (C) is in fluid communication with pad (212). The user may attach applicator (200) to container (C) via the threaded relationship between female threaded portion (206) of applicator (200) and male threading of container (C).

Figure 4B:
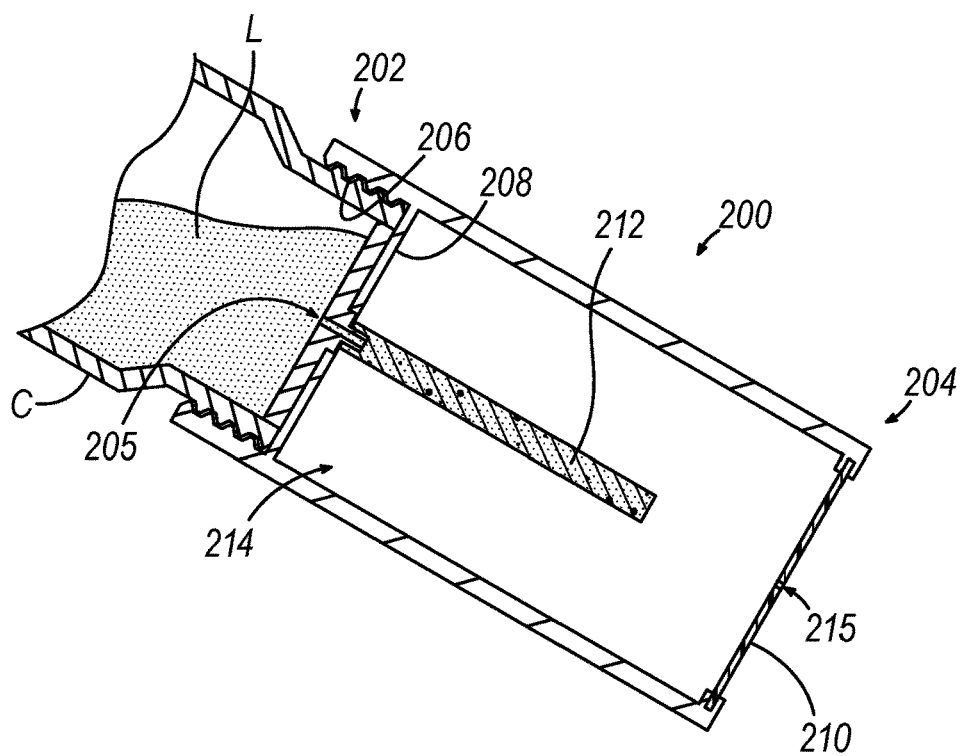
FIG. 4B depicts a cross-sectional view of the electro-lubricant applicator of FIG. 3, taken along a centerline thereof, coupled to a source of electro-lubricant in a downwardly tilted position.
Figure 4C:
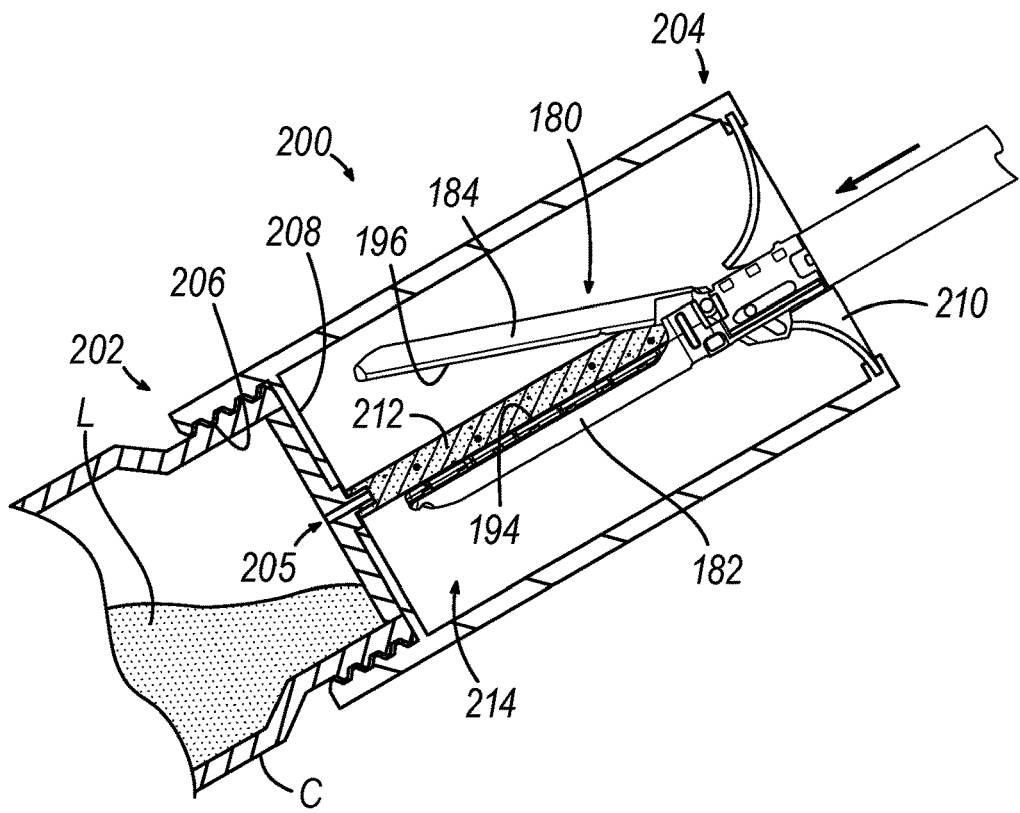
FIG. 4C depicts a cross-sectional view of the electro-lubricant applicator of FIG. 3, taken along a centerline thereof, coupled to a source of electro-lubricant in an upwardly tilted position, with the end effector of FIG. 2 in an open position and directly adjacent to an absorbent applicator pad of the electro-lubricant applicator.

Next, as shown in FIG. 4B, the user may tilt container (C) and applicator (200) such that gravity feeds electro-lubricant (L) into pad (212) via fluid pathway (205). The user may keep container and applicator (200) in the tilt position long enough until pad (212) absorbs a desirable amount of electro-lubricant (L). Once pad (212) has absorbed a sufficient amount of electro-lubricant (L), the user may insert end effector (180) into chamber (214) via expandable opening (215) of elastomeric seal (210) such that seal (210) expands from the normally closed configuration into the open configuration, as shown in FIG. 4C. The user may open jaws (182, 184) of end effector such that pad (212) is located within the confines of electrode surfaces (194, 196). Additionally, the user may insert end effector (180) far enough into chamber (214) such that the open end of pad (212) engages a tissue stop of end effector (180) (e.g., the most proximal portion of end effector (180) intended to engage grasped tissue while using end effector (180) in accordance with the description herein).

Figure 4D:
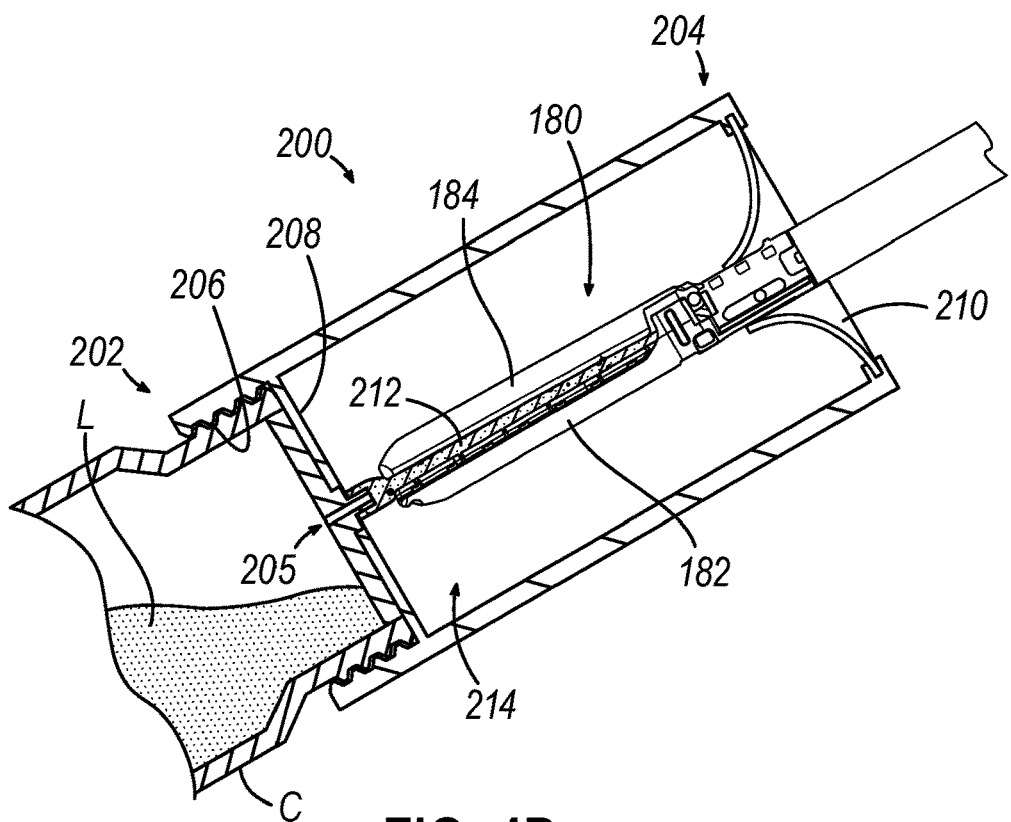
FIG. 4D depicts a cross-sectional view of the electro-lubricant applicator of FIG. 3, taken along a centerline thereof, coupled to a source of electro-lubricant in an upwardly tilted position, with the end effector of FIG. 2 grasping the absorbent applicator pad of FIG. 4C.
Figure 4E:
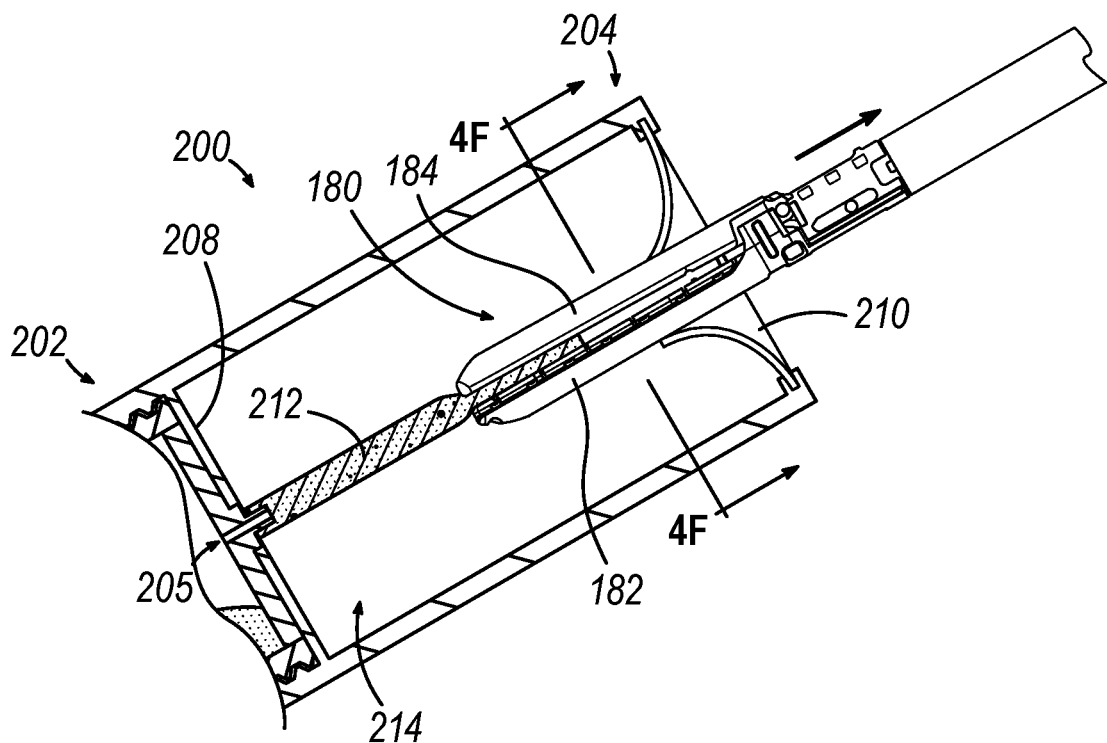
FIG. 4E depicts a cross-sectional view of the electro-lubricant applicator of FIG. 3, taken along a centerline thereof, coupled to a source of electro-lubricant in an upwardly tilted position, with the end effector of FIG. 2 grasping the absorbent applicator pad of FIG. 4C and being retracted away from the electro lubricant applicator.
Figure 4F:
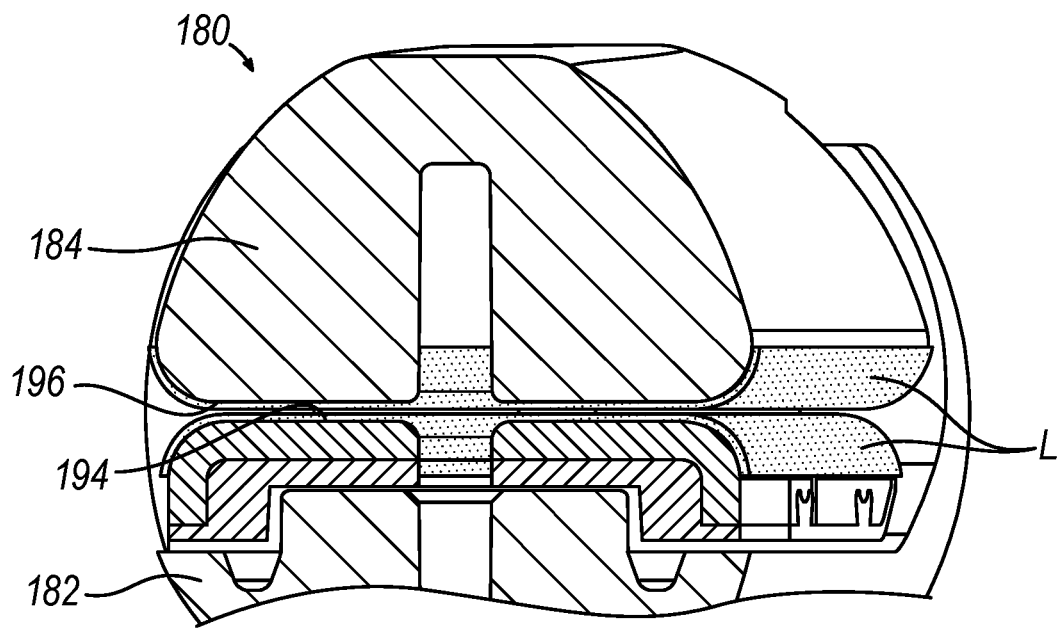
FIG. 4F depicts a cross-sectional view of the end effector of FIG. 2, taken along line 4F-4F of FIG. 4E, with a coating of electro-lubricant applied therefore.

As shown in FIG. 4D, the user may then suitably close jaws (182, 184) in accordance with the description herein such that electrode surfaces (194, 196) (and any other surface intended to be lubricated) engage pad (212) with sufficient pressure to transfer electro-lubricant (L) from pad (212) onto electrode surfaces (194, 196). Next, if desired, as shown in FIG. 4E, the user may retract end effector (180) away from applicator (200) while jaws (182, 184) are still closed to grasp pad (212). Sliding contact between jaws (182, 184) and pad (212) while end effector (180) is retracted may promote applying an even layer of electro-lubricant (L) (and removing excess electro-lubricant (L)) onto the intended surfaces (in this case electrode surfaces (194, 196) of end effector (180), as shown in FIG. 4F. Additionally, sliding contact between jaws (182, 184) and pad (212) while end effector (180) is retracted may promote the removal of accumulated eschar from jaws (182, 184). Therefore, the material forming pad (212) may have suitable abrasive characteristics configured to remove accumulated debris from jaws (182, 184) without undesirably damaging/scratching surfaces of jaws (182, 184). Therefore, a user may utilize applicator (200) in conjunction with a container (C) of electrosurgical (L) in order to apply an even layer of electro-lubricant (L) to end effector (180) and/or to remove accumulated eschar (or any other suitable debris) from jaws (182, 184.

In the present example, electro-lubricant applicator (200) is configured to couple to a source of electro-lubricant, such as an open-ended container (C) filled electro-lubricant (L), so absorbent applicator pad (212) may selectively absorb electro-lubricant (L) for use in accordance with the description herein. In some instances, it may be desirable to have an applicator that already contains electro-lubricant (L) such that there is no need to couple applicator with a container (C). Additionally, only portions of end effector (180) intended to grasp pad (212) receive an even coating of electro-lubricant. In some instances, it may be desirable to apply electro-lubricant (L) to more surfaces than those that just grasp pad (212).

FIGS. 5A-5G show an alternative electro-lubricant applicator (220) that may be used in replacement of applicator (200) and container (C) described above. Electro-lubricant applicator (220) may be substantially similar to applicator (200) described above, with differences elaborated below. Rather than having a cap body (201) configured to selectively couple to a container (C) of electro-lubricant (L), applicator (220) includes a container body (221) defining an internal chamber (234) that holds a suitable amount of electro-lubricant (L). Therefore, applicator (220) contains electro-lubricant (L) itself, rather than selectively coupling with a container (C) holding electro-lubricant (L).

Container body (221) extends from a bottom portion (222) to a top portion (224). Bottom portion (222) includes a floor (228) which partially defines internal chamber (234) housing an absorbent applicator pad (232). Floor (228) does not define a fluid pathway such that floor (228) is configured to help contain electro-lubricant (L) within internal chamber (234). Absorbent applicator pad (232) is attached to floor (228) and extends upwardly from floor (228) toward top portion (224) of applicator (220). Absorbent applicator pad (232) may be substantially similar to applicator pad (212) described above, with differences elaborated below.

As mentioned above, container body (221) defines internal chamber (234) holding a suitable amount of electro-lubricant (L). Absorbent applicator pad (232) is housed within internal chamber (234) such that pad (232) is suitably submerged within electro-lubricant (L). Absorbent applicator pad (232) is formed of a suitable material such that absorbent applicator pad (232) may absorb an electro-lubricant (L) and maintain its intended shape during storage and such that end effector (180) may grasp pad (232). Additionally, pad (232) is formed of a suitable material such that pad (232) may transfer absorbed electro-lubricant to jaws (182, 184) in response to end effector (180) grasping pad (232) with a suitable compressive force. As will be described in greater detail below, absorbent applicator pad (232) is configured to absorb a suitable amount of electro-lubricant (L) while maintaining its shape such that jaws (182, 184) of end effector (180) may grasp pad (232) in order to apply electro-lubricant (L) to electrode surfaces (194, 196).

Top portion (224) includes a male threaded portion (226) configured to selectively couple with an end cap (236). End cap (236) is configured to cover an elastomeric seal (230) containing electro-lubricant (L) prior to exemplary use of applicator (220) in accordance with the description above. Therefore, end cap (236) may prevent any unwanted objects from entering internal chamber (234) prior to intended use, as well as inadvertent disbursement of electro-lubricant (L) prior to intended use.

Top portion (224) also includes a top cover, currently in the form of an elastomeric seal (230) defining an expandable opening (235). In some instances, cover may be an absorbent material. Elastomeric seal (230) is located above pad (232) such that seal (230) partially defines internal chamber (234) housing pad (232) and electro-lubricant (L). Elastomeric seal (230) may be substantially similar to elastomeric seal (210) described above.

Expandable opening (235) of seal (230) is naturally in a closed configuration and further configured to expand into an open configuration in response to end effector (180) being inserted into chamber (234). In the closed configuration, elastomeric seal (230) may prevent unwanted fluid/materials from entering internal chamber (234). Additionally, while in the closed configuration, elastomeric seal (230) may prevent electro-lubricant (L) within chamber (234) from accidentally exiting chamber (234) via top portion (224). In the open configuration, expandable opening (235) of seal (230) is configured to expand to thereby accommodate the insertion of end effector (180) into chamber (234) of applicator (220) in accordance with the description herein. Seal (230) is resiliently biased toward the closed configuration. Therefore, in the expanded state, seal (230) is sufficiently resilient to conform to the outer surface of end effector (180) to inhibit transfer the fluid/minerals into and out of chamber (234), in a similar fashion to when seal (210) is in the closed configuration. Additionally, seal (230) may resiliently conform to the outer surfaces of end effector (180) in order to evenly apply electro-lubricant (L) accumulated on the outer surfaces of end effector (180) after being dipped into electro-lubricant (L) in accordance with the description herein.

Figure 5A:
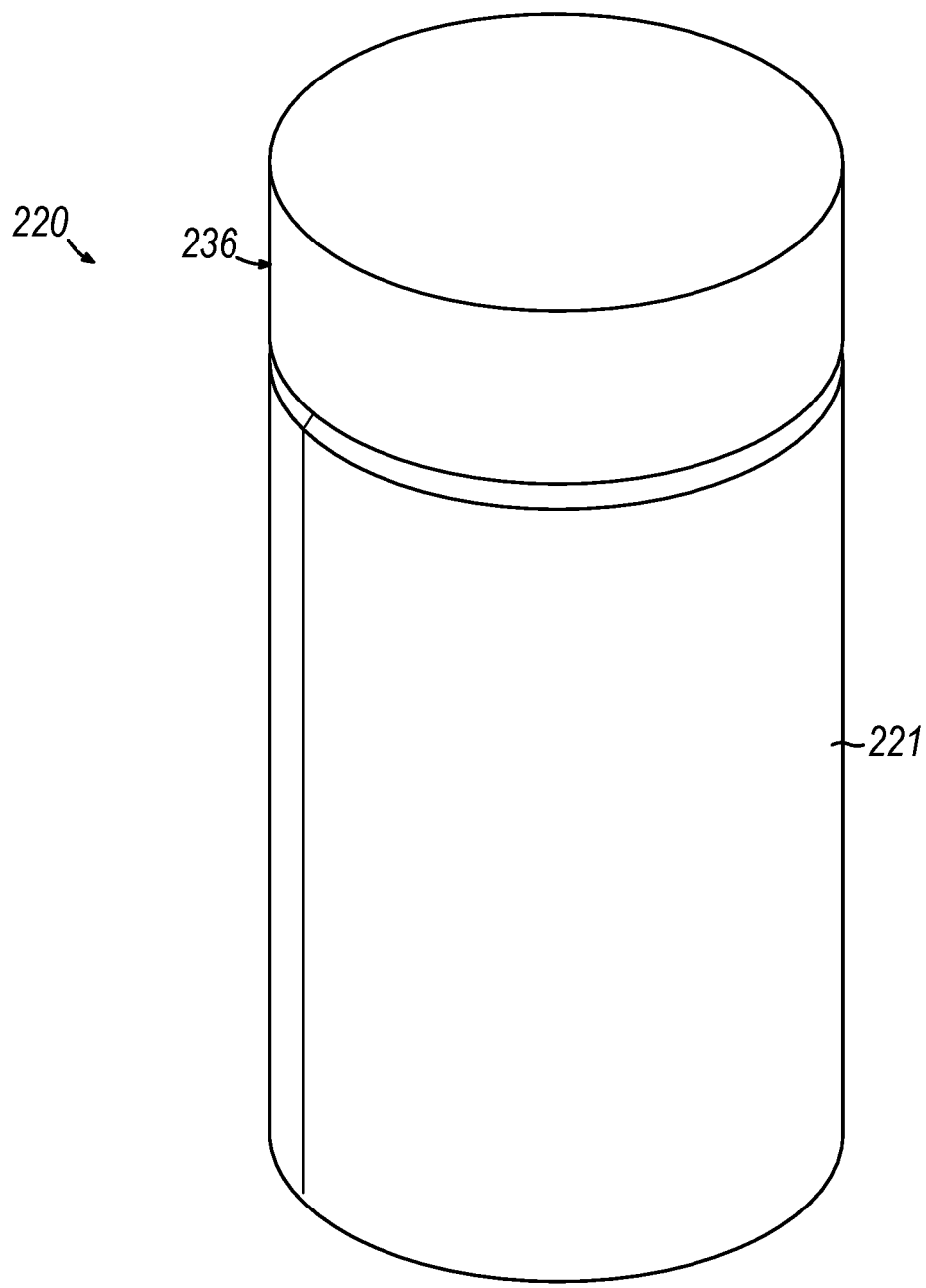
FIG. 5A depicts a perspective view of another electro-lubricant applicator.
Figure 5B:
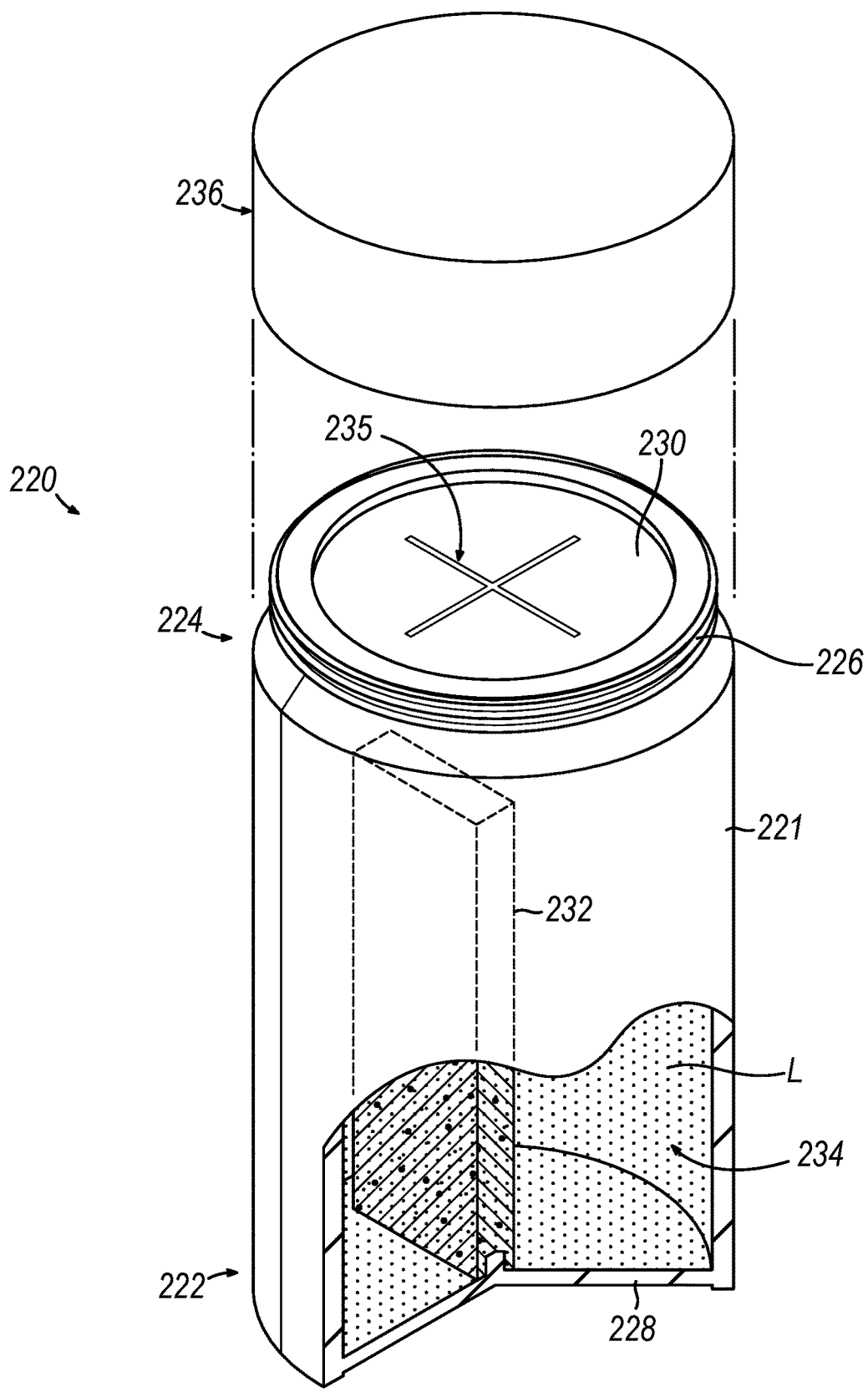
FIG. 5B depicts a partial sectional perspective view of the electro-lubricant applicator of FIG. 5A.
Figure 5C:
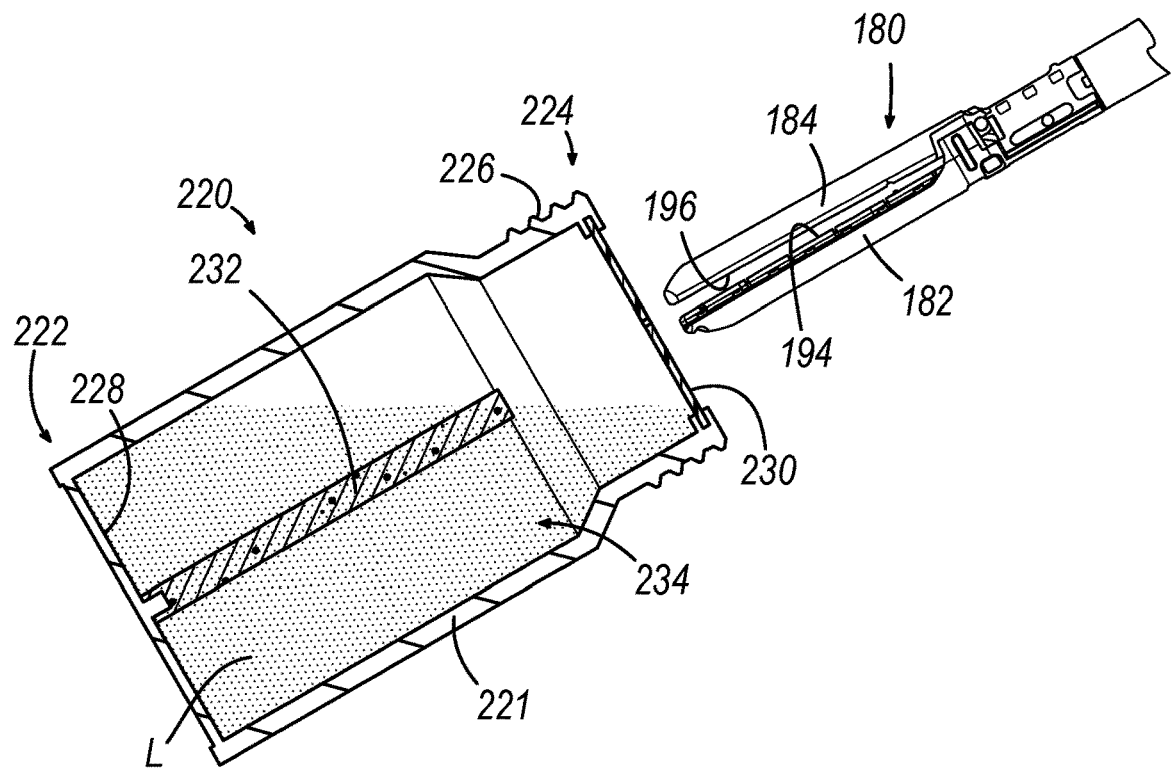
FIG. 5C depicts a cross-sectional view of the electro-lubricant applicator of FIG. 5A, taken along a centerline thereof, with the end effector of FIG. 2 directly adjacent thereto.
Figure 5D:
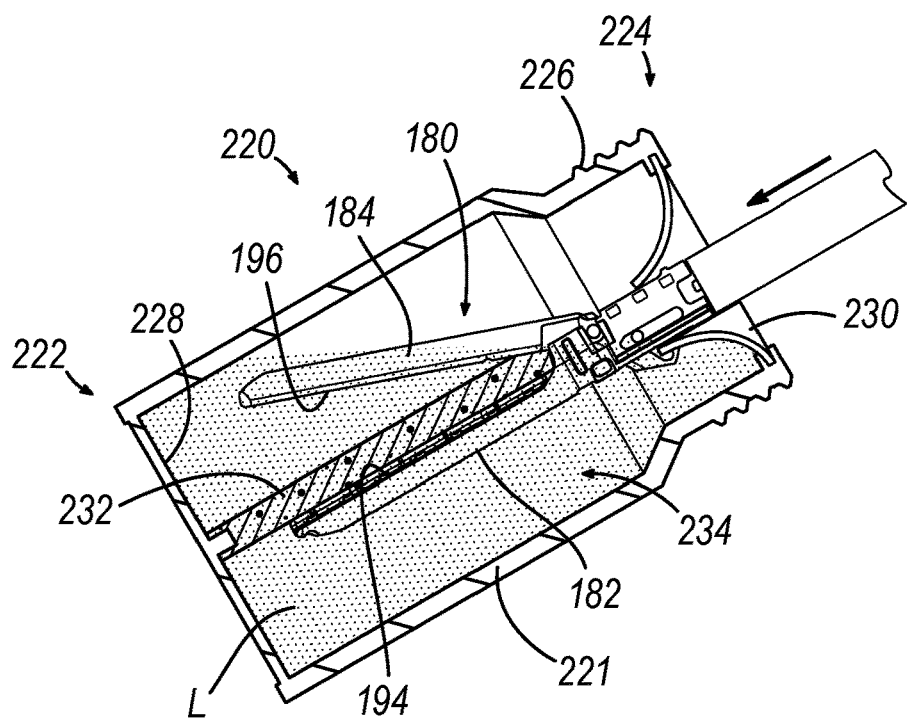
FIG. 5D depicts a cross-sectional view of the electro-lubricant applicator of FIG. 5A, taken along a centerline thereof, with the end effector of FIG. 2 in an open position and directly adjacent to an absorbent applicator pad of the electro-lubricant applicator.
Figure 5E:
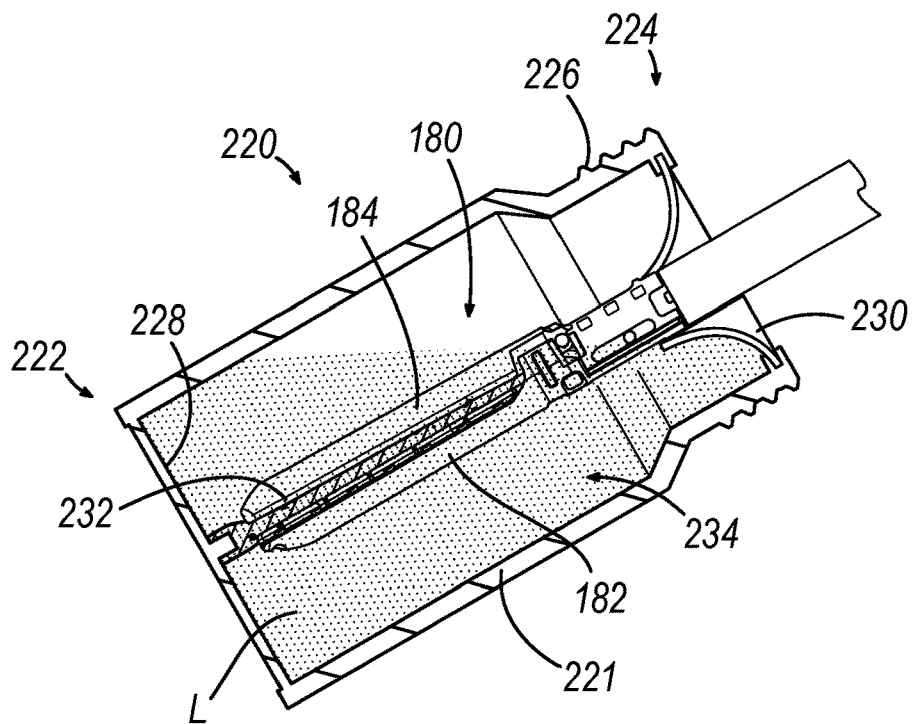
FIG. 5E depicts a cross-sectional view of the electro-lubricant applicator of FIG. 5A, taken along a centerline thereof, with the end effector of FIG. 2 grasping the absorbent applicator pad of FIG. 5D.

FIGS. 5C-5G show an example use of applicator (220) in order to apply an even coating of electro-lubrication to desired surfaces of end effector (180) in a reliable, effective, easy, and efficient manner. First, a user may remove end cap (236) from top portion (224) of container body (221) such that seal (230) is exposed, as shown in FIG. 5C. Next, as also shown in FIG. 5C, the user may align the distal end of end effector (180) with expandable opening (235) of seal (230). As shown in FIG. 5D, the user may insert end effector (180) into chamber (234) via expandable opening (235) of elastomeric seal (230) such that seal (230) expands from the normally closed configuration into the open configuration. It should be understood that at the moment shown in FIG. 5D, all suitable surfaces of end effector (180) intended to receive a coating of electro-lubricant (L) are submerged in electro-lubricant (L). The user may open jaws (182, 184) of end effector such that pad (232) it located within the confines of electrode surface (194, 196). Additionally, the user may insert end effector (180) far enough into chamber (234) such that the open end of pad (232) engages a tissue stop of end effector (180) (e.g., the most proximal portion of end effector (180) intended to engage grasped tissue while using end effector (180) in accordance with the description herein.

Figure 5F:
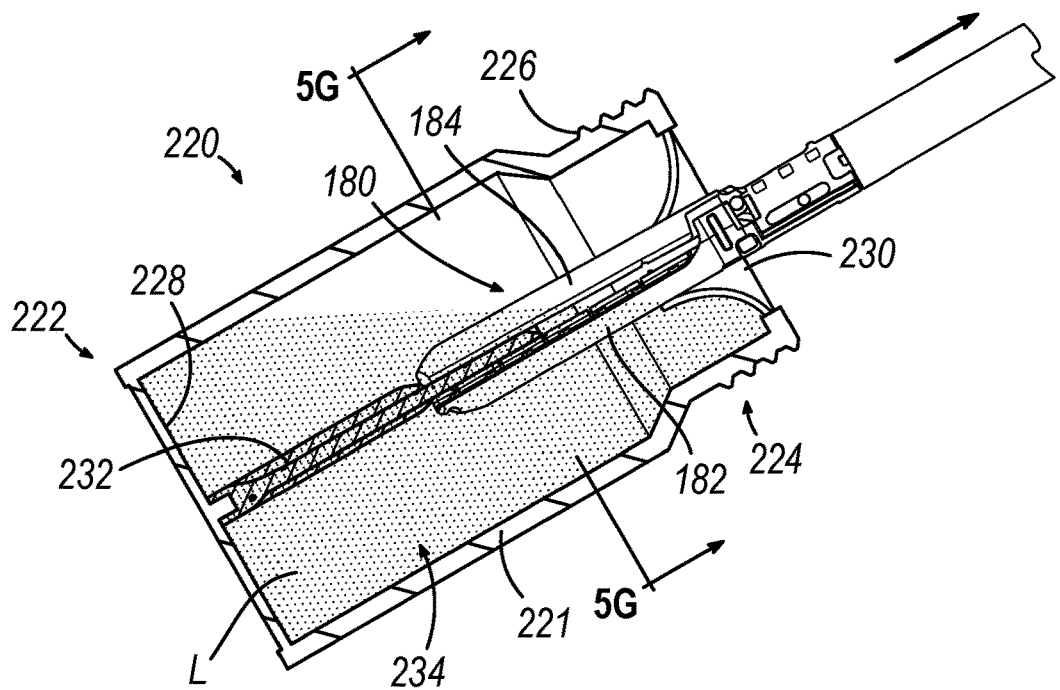
FIG. 5F depicts a cross-sectional view of the electro-lubricant applicator of FIG. 5A, taken along a centerline thereof, with the end effector of FIG. 2 grasping the absorbent applicator pad of FIG. 5D and being retracted away from the electro lubricant applicator.
Figure 5G:
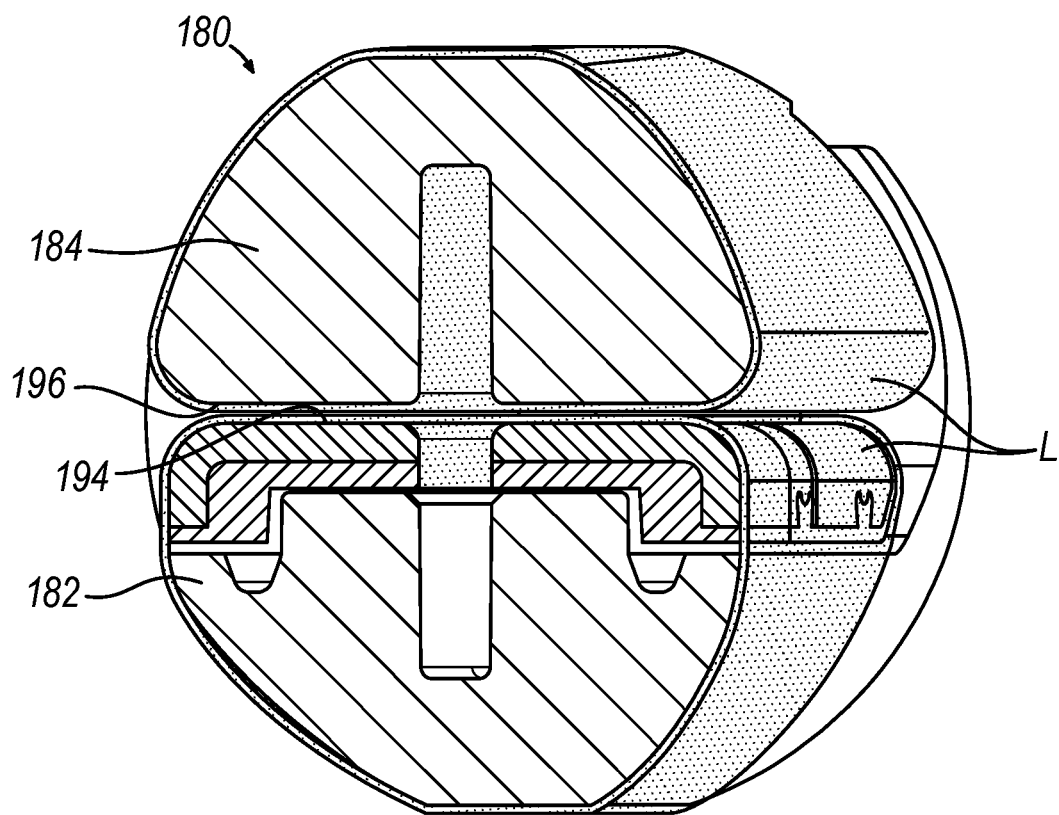
FIG. 5G depicts a cross-sectional view of the end effector of FIG. 2, taken along line 5G-5G of FIG. 5F, with a coating of electro-lubricant applied thereto.

As shown in FIG. 5F, the user may then suitably close jaws (182, 184) in accordance with the description herein such that electrode surfaces (194, 196) (and any other surface intended to be lubricated) engage pad (232) with sufficient pressure to transfer electro-lubricant (L) from pad (232) onto electrode surfaces (194, 196). Next, as shown in FIG. 5F, the user may retract end effector (180) away from applicator (220) while jaws (182, 184) are still closed to grasp pad (232). Sliding contact between jaws (182, 184) and pad (232) while end effector (180) is retracted may promote applying an even layer of electro-lubricant (L) onto electrode surfaces (194, 196) of end effector (180), as shown in FIG. 5G. Additionally, contact between the outer surfaces of jaws (182, 184) and seal (230) as end effector is retracted may promote applying an even layer of electro-lubricant (L) onto the outer surface of jaws (182, 184). Therefore, a user may utilize applicator (220) to apply an even layer of electro-lubricant (L) to end effector (180). Additionally, sliding contact between jaws (182, 184) and pad (232) while end effector (180) is retracted may promote the removal of accumulated eschar from jaws (182, 184). Therefore, the material forming pad (232) may have suitable abrasive characteristics configured to remove accumulated debris from jaws (182, 184) without undesirably damaging/scratching surfaces of jaws (182, 184).

As mentioned above, elastomeric seal (230) and pad (232) are utilized to apply electro-lubricant (L) to the surfaces of jaws (182, 184) for an even coating. In some instances, it may be desirable to have an applicator pad that is specifically dimensioned to suitably engage all the desirable surfaces of jaws (182, 184) and electrode surfaces (194, 196) to apply an even coating of electro-lubricant (L) on such surfaces.

Figure 6:
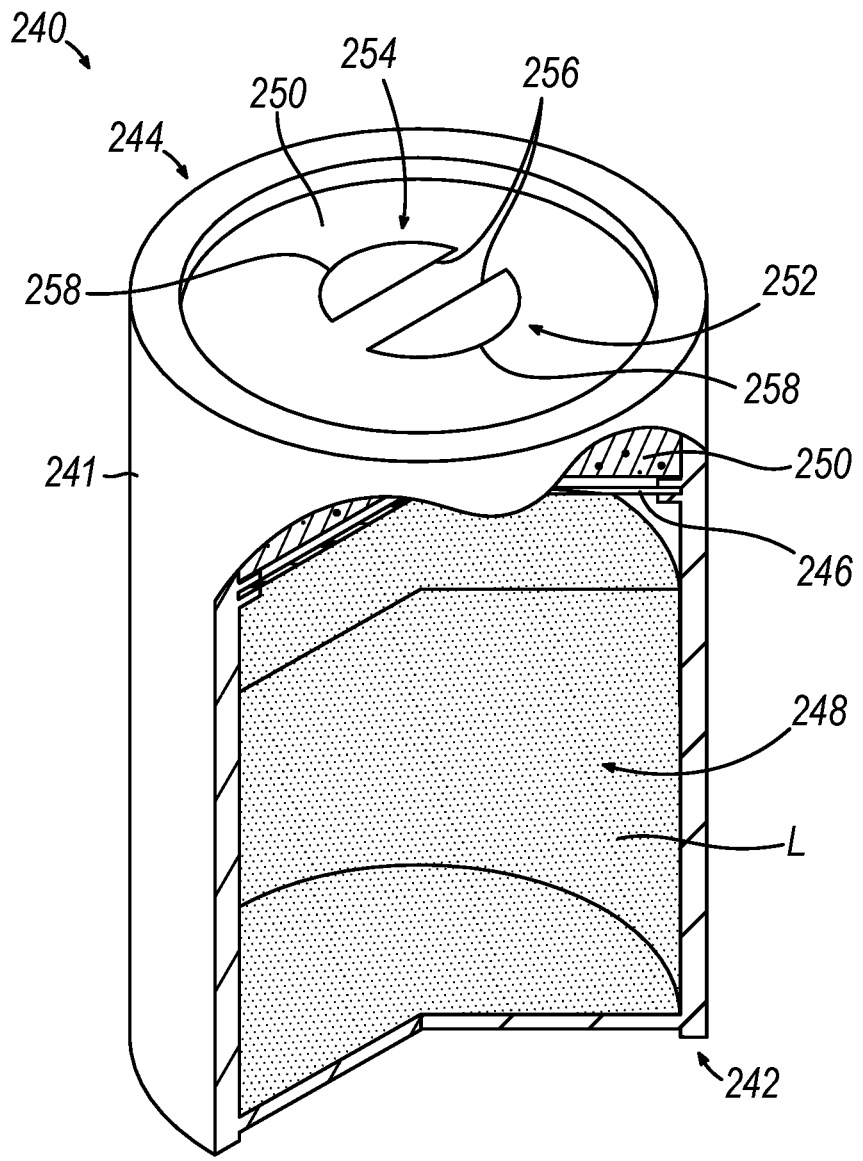
FIG. 6 depicts a partial sectional perspective view of an exemplary electro-lubricant applicator.
Figure 7A:
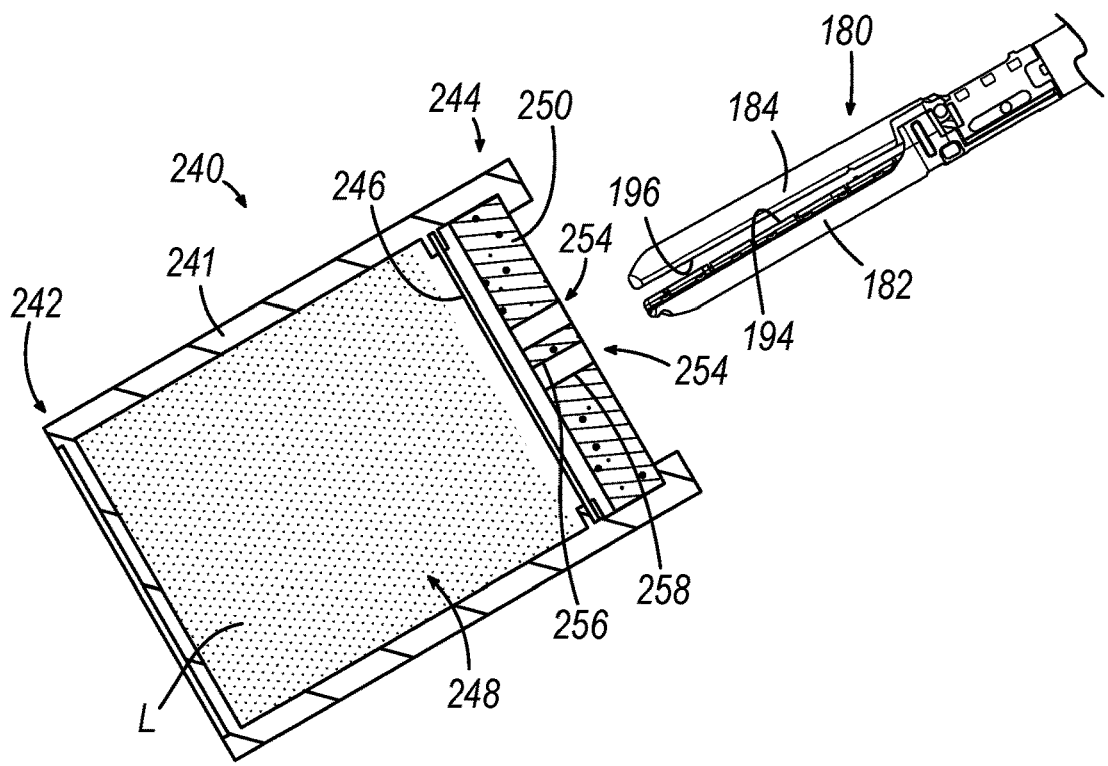
FIG. 7A depicts a cross-sectional view of the electro-lubricant applicator of FIG. 6, taken along a centerline thereof, with the end effector of FIG. 2 proximate thereto.
Figure 7B:
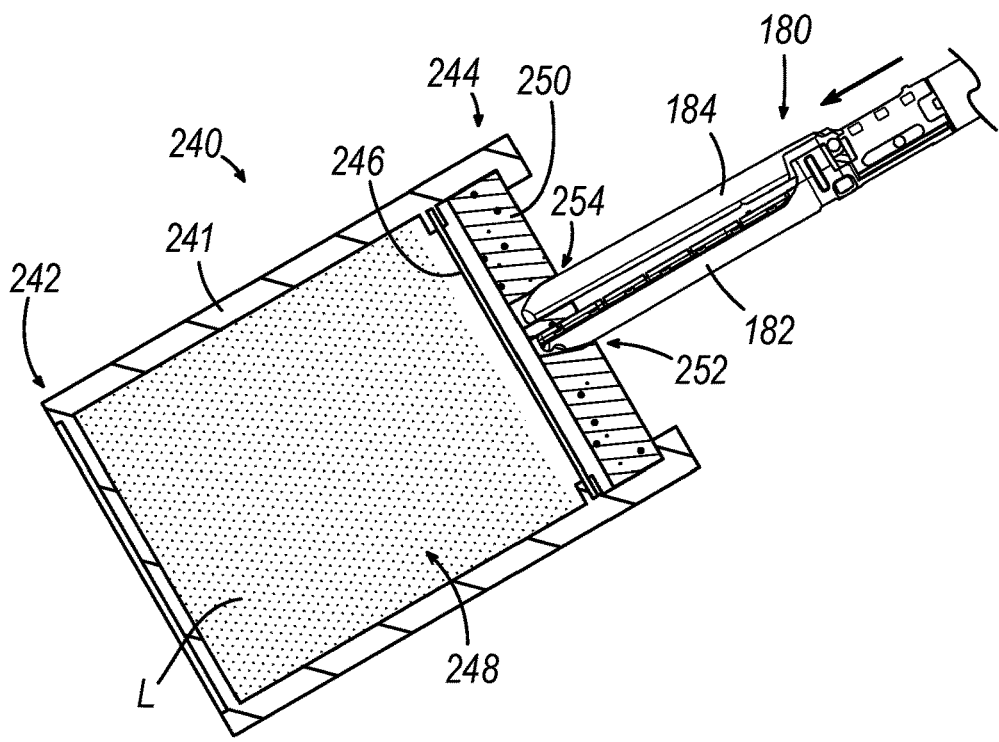
FIG. 7B depicts a cross-sectional view of the electro-lubricant applicator of FIG. 6, taken along a centerline thereof, with the end effector of FIG. 2 being initially inserted into the electro-lubricant applicator.
Figure 7C:
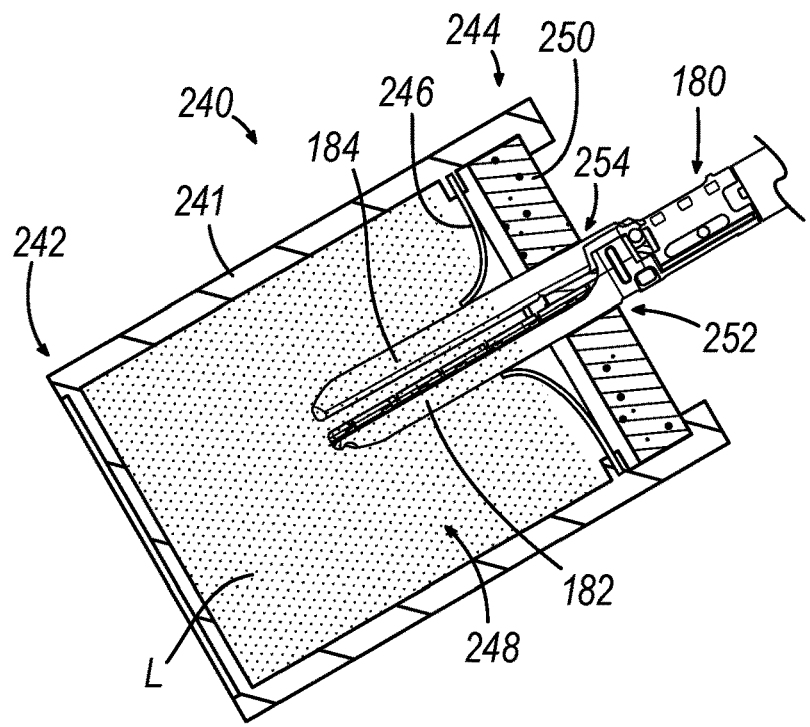
FIG. 7C depicts a cross-sectional view of the electro-lubricant applicator of FIG. 6, taken along a centerline thereof, with the end effector of FIG. 2 being fully inserted into the electro-lubricant applicator.
Figure 7D:
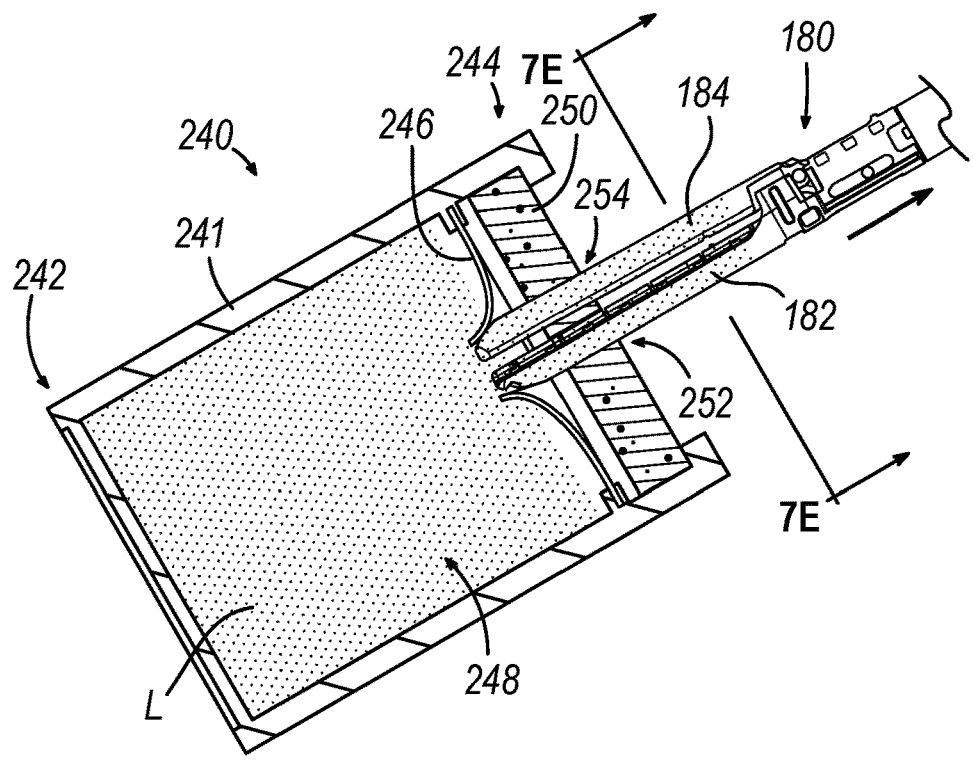
FIG. 7D depicts a cross-sectional view of the electro-lubricant applicator of FIG. 6, taken along a centerline thereof, with the end effector of FIG. 2 being retracted from the electro-lubricant applicator.

FIGS. 6-7D show another alternative electro-lubricant applicator (240) that may be used in replacement of applicator (220). Electro-lubricant applicator (240) may be substantially similar to applicator (220) described above, with differences elaborated below. Rather than having a pad (232) and a seal (230) apply an even coating to electrode surfaces (194, 196) and outer surfaces of jaws (182, 184), respectively, applicator (240) includes an applicator pad (250). Applicator pad (250) includes complementary surface (256, 258) dimensioned to engage jaws (182, 184) as they are retracted from a reservoir of electro-lubricant in order to spread an even layer of electro-lubricant (L) end effector (180).

Container body (241) extends from a bottom portion (242) to a top portion (244). Container body (241) defines an internal chamber (248) which houses a reservoir of electro-lubricant (L). A penetrable containment layer (246) is interposed between applicator pad (250) and electro-lubricant (L). Containment layer (246) is configured to prevent electro-lubricant (L) housed within chamber (248) from inadvertently escaping prior to intended use of applicator (240). However, containment layer (246) is also configured to be penetrated by insertion of end effector (180) into chamber (248) such that layer (246) does not prevent end effector (180) from accessing electro-lubricant (L). Containment layer (246) may be formed of any suitable material as would be apparent to one skilled in the art in view of the teachings herein. For example, containment layer (246) may include a thin foil layer.

Top portion (244) includes applicator pad (250). Applicator pad (250) defines a first jaw opening (252) and a second jaw opening (254), each dimension to receive a respective jaw (182, 184). In particular, jaw openings (252, 254) extend through pad (250), as shown in FIGS. 7A-7D, such that jaws (182, 184) of end effector (180) may be inserted through pad (250) via openings (252, 254). Openings (252, 254) are each defined by an electrode engagement surface (256) and an outer jaw engagement surface (258). Electrode engagement surfaces (256) are configured to abut against a respective electrode surface (194, 196) as end effector (180) is both inserted into chamber (248) and retracted out of chamber (248). Similarly, outer jaw engagement surfaces (258) are configured to abut against outer surfaces of a respective jaw (182, 184) as end effector (180) is both inserted into chamber (248) and retracted out of chamber (248). Contact between jaws (182, 184) of end effector (180) and engagement surfaces (256, 268) is configured to evenly apply a layer of electro-lubricant (L) onto surfaces of jaws (182, 184) after being dipped into the reservoir of electro-lubricant (L) within chamber (248).

Openings (252, 254) may be dimensioned slightly smaller than the cross-sectional dimensioned of jaws (182, 184) in order to ensure contact between jaws (182, 184) and surfaces (256, 258). In such instances, pad (250) may be formed of a resilient material that may expand as a result of jaws (182, 184) engagement with surfaces (256, 258). Additionally, pad (250) may be sufficiently resilient such that openings (252, 254) may return to their original dimensions after jaws (182, 184) are fully retracted from applicator (240).

Figure 7E:
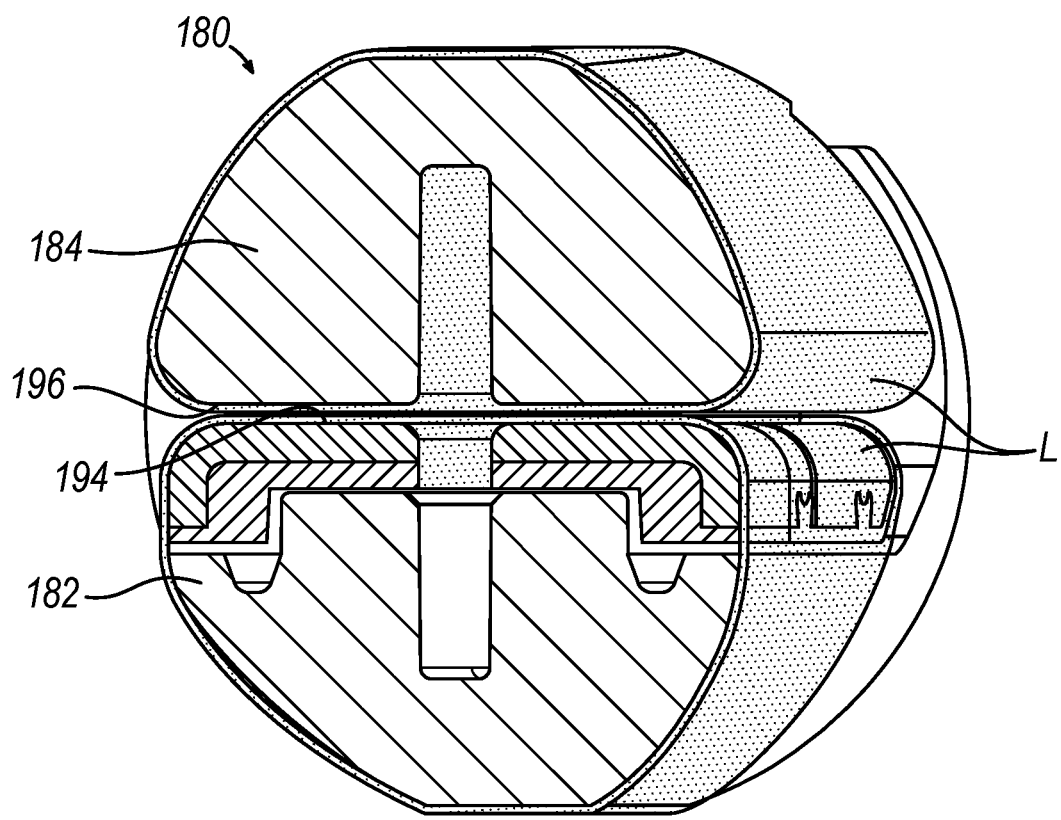
FIG. 7E depicts a cross-sectional view of the end effector of FIG. 2, taken along line 7E-7E of FIG. 7D, with a coating of electro-lubricant applied thereto.

FIGS. 7A-7E show an exemplary use of applicator (240) in order to apply an even coating of electro-lubrication to desired surfaces of end effector (180) in a reliable, effective, easy, and efficient manner. First, the user may align the distal end of end effector (180) with openings (252, 254) of applicator pad (250), as shown in FIG. 7A. Next, the user may initially insert end effector (180) into openings (252, 254) of pad (250) such that a distal end of end effector (180) is adjacent to containment layer (246), as shown in FIG. 7B. Next, the user may further insert end effector (180) into openings (252, 254) of pad (250) such that a distal end of end effector (180) penetrates containment layer (246) and suitable portions of end effector (180) are within electro-lubricant (L), as shown in FIG. 7C. With suitable portions of end effector (180) coated with electro-lubricant (L), the user may then retract end effector (180) out of chamber (248) such that engagement surfaces (256, 258) spread an even layer of electro-lubricant (L) onto suitable portions of end effector (180), as shown in FIGS. 7D-7E. Additionally, sliding contact between jaws (182, 184) and pad (250) while end effector (180) is retracted may promote the removal of accumulated eschar from jaws (182, 184). Therefore, the material forming pad (250) may have suitable abrasive characteristics configured to remove accumulated debris from jaws (182, 184) without undesirably damaging/scratching surfaces of jaws (182, 184).

Figure 8:
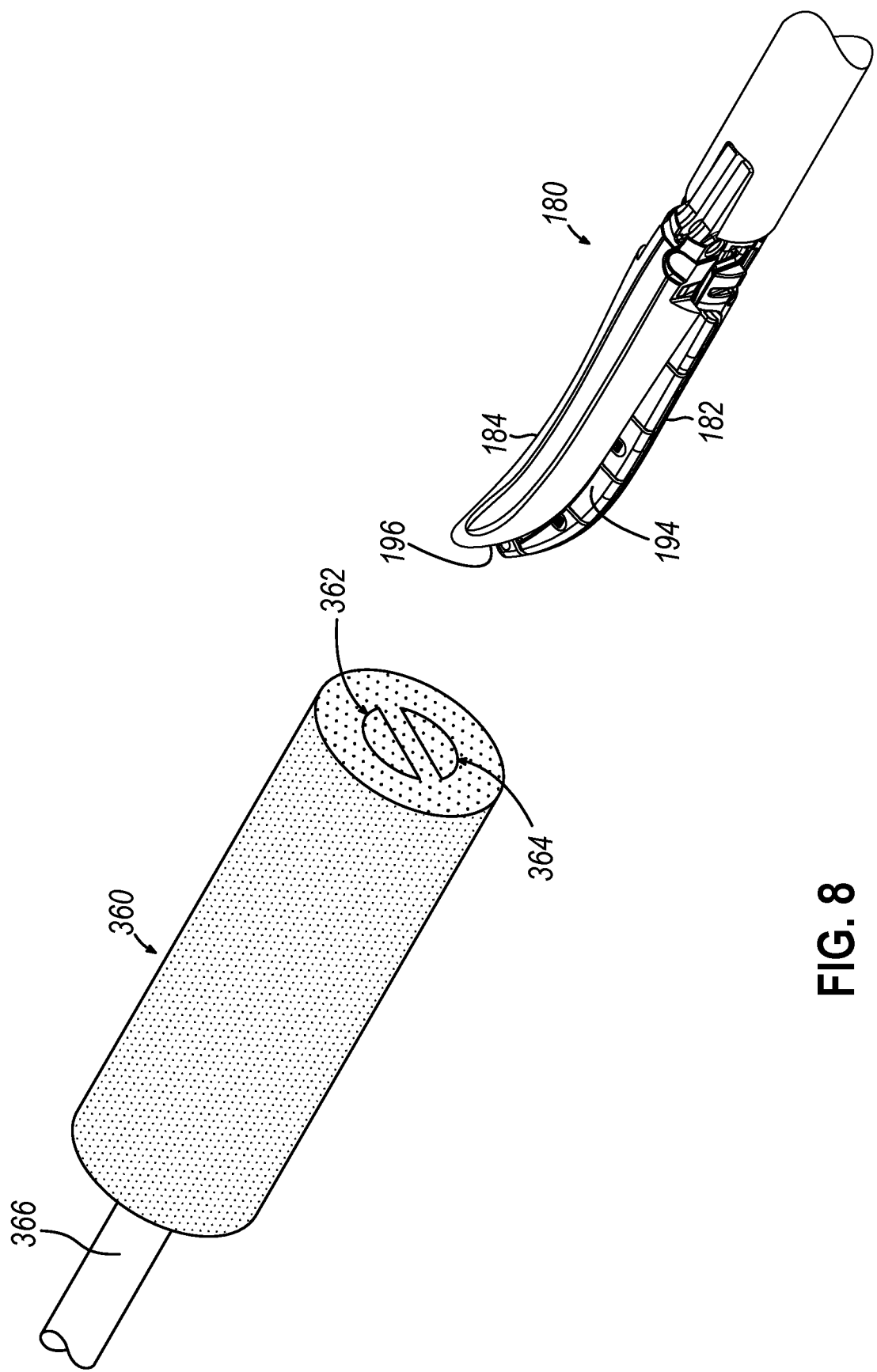
FIG. 8 depicts a perspective view of an exemplary electro-lubricant pad with the end effector of FIG. 2 proximate thereto.
Figure 9A:
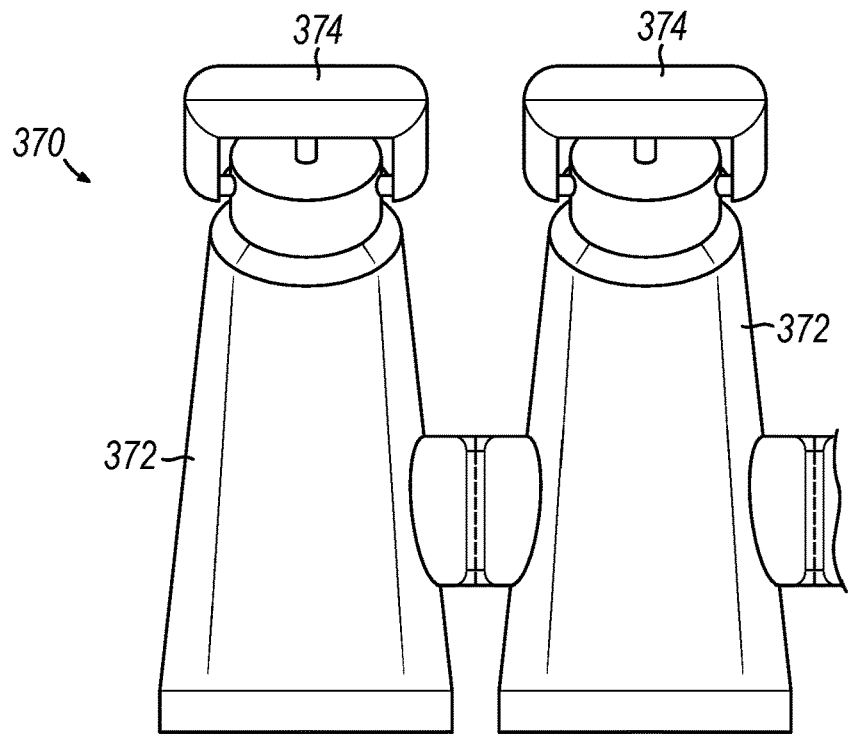
FIG. 9A depicts a perspective view of an exemplary electro-lubricant applicator with a single-use cap attached thereto.
Figure 9B:
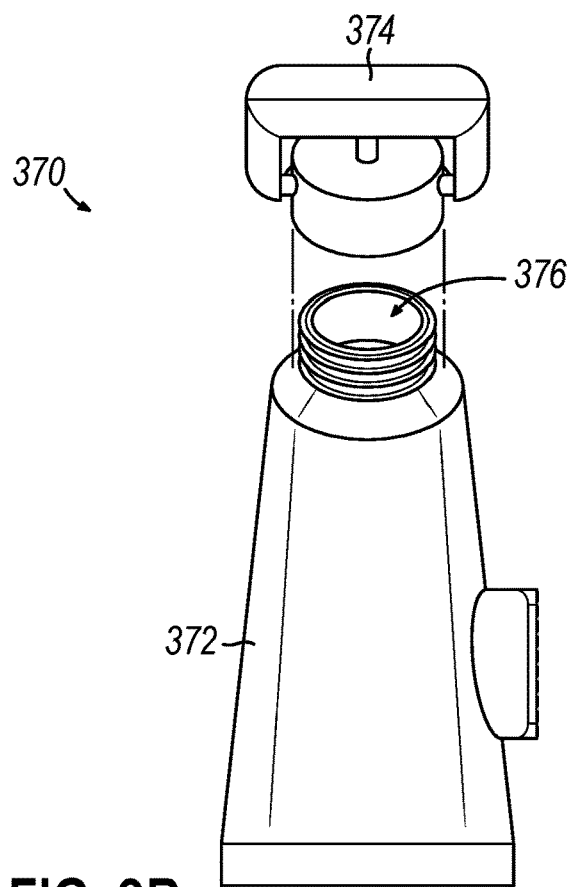
FIG. 9B depicts a perspective view of the electro-lubricant applicator of FIG. 9A with the single-use cap removed.

FIG. 8 shows yet another alternative applicator pad (360) that may be used on its own to spread an even layer of electro-lubricant (L) already applied to suitable portions of end effector (180); while FIGS. 9A-9B0 show a controlled application tube (370) configured to controllably apply electro-lube (L) onto selected portions of end effector (180). While applicator pad (360) and application tube (370) are described herein as being used together, it should be understood that applicator pad (260) and application tube (370) may be utilized separately as would be apparent to one skilled in the art in view of the teachings herein.

Pad (360) is similar to pad (250) described above, except pad (360) is longer. Pad (360) defines openings (362, 364) that are suitably long such that jaws (182, 184) of end effector (180) may be inserted and suitably housed within openings (362, 364). Therefore, jaws (182, 184) with electro-lube (L) initially applied thereto may be inserted into openings (362, 364) such that pad (360) spreads the electro-lube (L) into an even layer onto jaws (182, 184). Pad (360) may be attached to a control rod (366) that a user may utilize in order to control pad (360) during exemplary use in accordance with the description herein.

Controlled application tube (370) includes a squeeze tube (372) filled with electro-lube (L) and a one-time use cap (374). Squeeze tube (372) includes an open end (376) that is covered by one-time use cap (374). One-time use cap (374) may prevent inadvertent escape of electro-lube (L) out of open end (376) before intended use of application tube (370) in accordance with the description herein. However, once removed, one-time use cap (374) may not be reattached to open end (376), thereby helping prevent tube (370) from being re-used across multiple procedures.

Figure 9C:
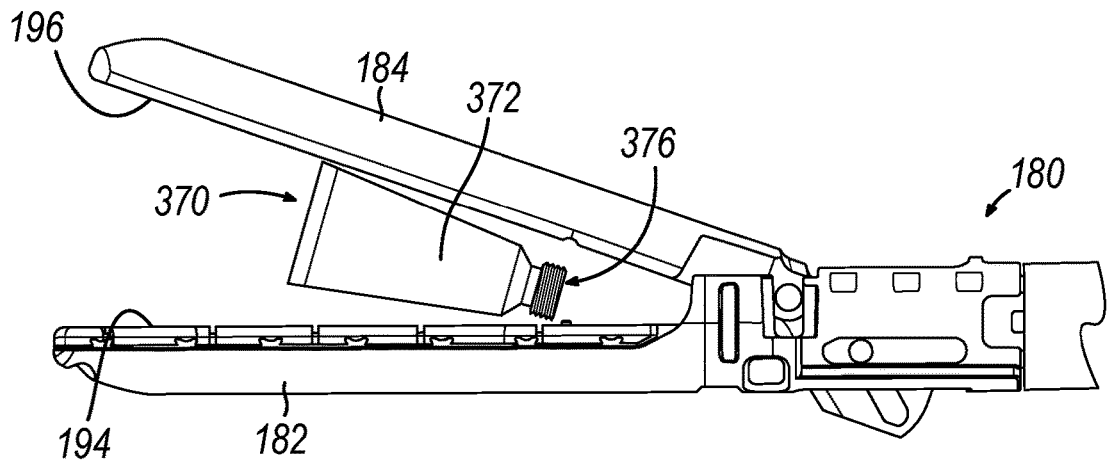
FIG. 9C depicts an elevational side view of the electro-lubricant applicator of FIG. 9A about to apply electro-lubricant to the end effector of FIG. 2.
Figure 9D:
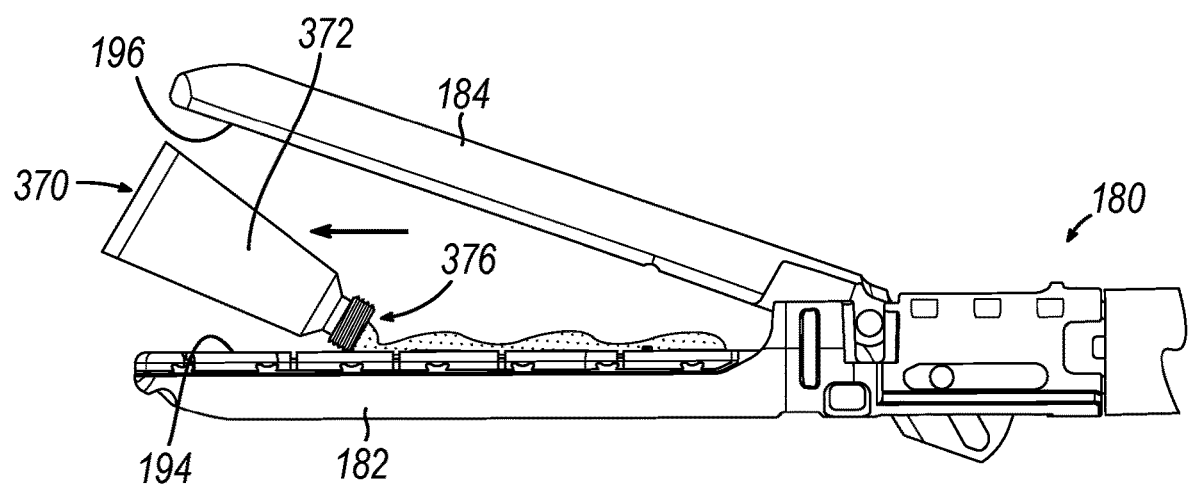
FIG. 9D depicts an elevational side view of the electro-lubricant applicator of FIG. 9A applying electro-lubricant to the end effector of FIG. 2.
Figure 9E:
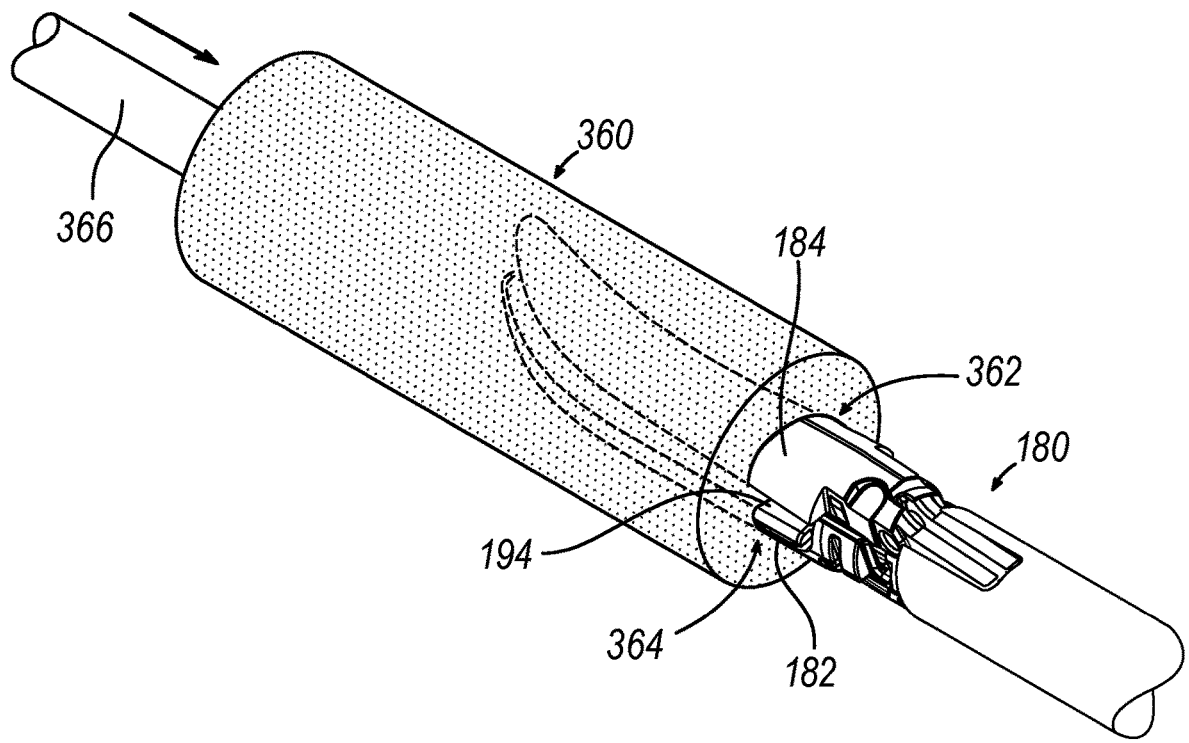
FIG. 9E depicts a perspective view of the end effector of FIG. 2 being inserted into the electro-lubricant pad of FIG. 8.
Figure 9F:
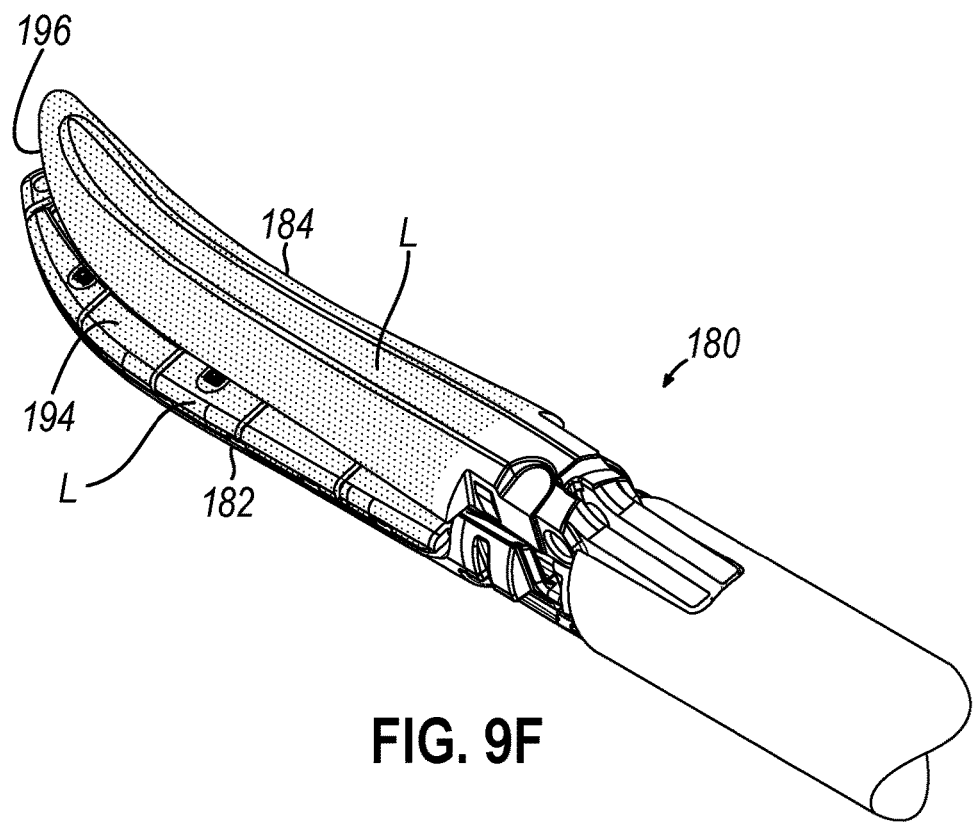
FIG. 9F depicts a perspective view of the end effector of FIG. 2 with electro-lubricant applied thereto.

Squeeze tube (372) may be formed of a suitable material such that once cap (374) is removed, the user may apply pressure to squeeze tube (372) such that electro-lube (L) controllable exits open end (376). Therefore, as user may controllably apply how much electro-lube (L) exits tube (372); open end (376) may allow the user to control where electro-lube (L) is applied in an accurate manner. FIGS. 9C-9D show an exemplary use of application tube (370) applying electro-lube (L) onto desired portions of end effector (180). As shown in FIG. 9C, a user may place open end (376) adjacent to where they desire electro-lube (L) to be applied. Next, as shown in FIG. 9D, the user may squeeze tube (372) such that electro-lube (L) controllably exits open end (376) onto the desired surfaces of end effector (180). With electro-lube (L) suitably applied to end effector (180), the use may insert jaws (182, 184) of end effector (180) into application pad (360) in order to spread electro-lube (L) into an even coat on jaws (182, 184), as shown between FIGS. 9E-9F.

While application pad (360) is used in the current example to apply an even coat of electro-lube (L) on jaws (182, 184), any other suitably means may be utilized as would be apparent to one skilled in the art in view of the teachings herein. For example, a flattened, spatula like body may be utilized to spread electro-lube (L) onto end effector (180).

III. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) an external body extending between a bottom end and a top end, wherein the external body defines an internal cavity; (b) a floor attached to the external body; (c) an applicator pad extending from the floor into the internal cavity defined by the external body, wherein the applicator pad comprises an absorbent material configured to absorb an electro-lubricant, wherein the applicator pad is dimensioned to be grasped by a pair of jaws of a surgical instrument; and (d) a cover associated with the top end of the external body, wherein the cover partially defines the internal cavity of the external body, wherein cover is configured to allow the pair of jaws to enter the internal cavity via the cover to grasp the applicator pad.

Example 2

The apparatus of any one or more of the preceding Examples, wherein the bottom end of the external body comprises a fluid source coupling feature configured to selectively couple the external body with a container housing the electro-lubricant.

Example 3

The apparatus of any one or more of the preceding Examples, wherein the fluid source coupling feature comprises a threaded section.

Example 4

The apparatus of any one or more of the preceding Examples, wherein the floor defines a fluid pathway in fluid communication with the applicator pad.

Example 5

The apparatus of any one or more of the preceding Examples, wherein the cover defines an expandable opening.

Example 6

The apparatus of any one or more of the preceding Examples, wherein the cover comprises a seal configured to transition between a normally closed position and an open position to allow the pair of jaws to enter the internal cavity.

Example 7

The apparatus of any one or more of the preceding Examples, wherein the seal comprises an elastomeric material.

Example 8

The apparatus of any one or more of the preceding Examples, wherein the seal comprises a duckbill valve.

Example 9

The apparatus of any one or more of the preceding Examples, wherein the internal cavity houses a reservoir of electro-lubricant.

Example 10

The apparatus of any one or more of the preceding Examples, further comprising a removable cap configured to selectively couple with the top end of the external body.

Example 11

The apparatus of any one or more of the preceding Examples, wherein the top end of the external body comprises a threaded section configured to couple with the removeable cap.

Example 12

The apparatus of any one or more of the preceding Examples, wherein the cover is configured to engage an outer surface of the pair of jaws while exiting the internal cavity.

Example 13

The apparatus of any one or more of the preceding Examples, wherein the cover is configured to spread an even layer of electro-lubricant onto the outer surface of the pair of jaws while exiting the internal cavity.

Example 14

The apparatus of any one or more of the preceding Examples, wherein the external body comprises a cylindrical shape.

Example 15

The apparatus of any one or more of the preceding Examples, wherein the floor defines a portion of the internal cavity.

Example 16

An apparatus, comprising: (a) an external body extending between a bottom end and a top end, wherein the external body defines an internal cavity housing a reservoir of electro-lubricant; (b) a floor attached to the external body; and (c) an applicator pad associated with the top end of the external body, wherein the applicator pad defines an opening dimensioned to receive at least one jaw of a surgical instrument such that the jaw may enter the internal cavity of the external body, wherein a portion of the applicator pad defining the opening is configured to engage the jaw while entering the internal cavity to thereby spread an even layer of electro-lubricant onto a surface of the jaw.

Example 17

The apparatus of any one or more of the preceding Examples, further comprises a containment layer interposed between the applicator pad and the reservoir of electro-lubricant.

Example 18

The apparatus of any one or more of the preceding Examples, wherein the containment layer comprises a foil material.

Example 19

A method of applying an electro-lubricant to an electrode surface of an electrosurgical instrument, the method comprising: (a) removing a cap from an open end of a squeeze tube filled with electro-lubricant; (b) placing the open end of the squeeze tube adjacent to the electrode surface of the electrosurgical instrument; (c) applying pressure to an outer surface of the squeeze tube until electro-lubricant exits the open end of the squeeze tube; and (d) while the electro-lubricant exits the open end of the squeeze tube, moving the open end of the squeeze tube along a length of the electrode surface.

Example 20

The method of any one or more of the preceding Examples, further comprising spreading the electro-lubricant onto the electrode surface as an even layer.

IV. Miscellaneous

It should be understood that any of the versions of the instruments and accessories described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. patent application Ser. No. 17/721,407, entitled "Applicator for Surgical Instrument Lubricant," filed on Apr. 15, 2022, published as U.S. Pat. Pub. No. 2023/0329742 on Oct. 19, 2023, the disclosure of which is incorporated by reference herein.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein, in its entirety.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an external body extending between a bottom end and a top end, wherein the external body defines an internal cavity;
   (b) a floor attached to the external body;
   (c) an applicator pad extending from the floor into the internal cavity defined by the external body, wherein the applicator pad comprises an absorbent material configured to absorb an electro-lubricant, wherein the applicator pad is dimensioned to be grasped by a pair of jaws of a surgical instrument; and
   (d) a cover associated with the top end of the external body, wherein the cover partially defines the internal cavity of the external body, wherein cover is configured to allow the pair of jaws to enter the internal cavity via the cover to grasp the applicator pad, wherein the cover defines an expandable opening.

2. The apparatus of claim 1, wherein the bottom end of the external body comprises a fluid source coupling feature configured to selectively couple the external body with a container housing the electro-lubricant.

3. The apparatus of claim 2, wherein the fluid source coupling feature comprises a threaded section.

4. The apparatus of claim 2, wherein the floor defines a fluid pathway in fluid communication with the applicator pad.

5. The apparatus of claim 1, wherein the cover comprises a seal configured to transition between a normally closed position and an open position to allow the pair of jaws to enter the internal cavity.

6. The apparatus of claim 5, wherein the seal comprises an elastomeric material.

7. The apparatus of claim 1, wherein the cover comprises an absorbent material.

8. The apparatus of claim 1, wherein the internal cavity houses a reservoir of electro-lubricant.

9. The apparatus of claim 8, further comprising a removable cap configured to selectively couple with the top end of the external body.

10. The apparatus of claim 9, wherein the top end of the external body comprises a threaded section configured to couple with the removeable cap.

11. The apparatus of claim 8, wherein the cover is configured to engage an outer surface of the pair of jaws while exiting the internal cavity.

12. The apparatus of claim 1, wherein the external body comprises a cylindrical shape.

13. The apparatus of claim 1, wherein the floor defines a portion of the internal cavity.

14. An apparatus, comprising:
(a) an external body extending between a bottom end and a top end, wherein the external body defines an internal cavity;
(b) a floor attached to the external body;
(c) an applicator pad extending from the floor into the internal cavity defined by the external body, wherein the applicator pad comprises an absorbent material configured to absorb an electro-lubricant, wherein the applicator pad is dimensioned to be grasped by a pair of jaws of a surgical instrument; and
(d) a cover attached with the top end of the external body, wherein the cover partially defines the internal cavity of the external body, wherein cover is configured to allow the pair of jaws to enter the internal cavity via the cover, while the cover remains attached with the top end of the external body, to grasp the applicator pad.

15. The apparatus of claim 14, wherein the cover comprises an expandable seal that allows the part of jaws to enter the internal cavity.

16. An apparatus, comprising:
(a) an external body extending between a bottom end and a top end, wherein the external body defines an internal cavity;
(b) a floor attached to the external body;
(c) an applicator pad extending from the floor into the internal cavity defined by the external body, wherein the applicator pad comprises an absorbent material configured to absorb an electro-lubricant, wherein the applicator pad is dimensioned to be grasped by a pair of jaws of a surgical instrument; and
(d) a cover associated with the top end of the external body, wherein the cover partially defines the internal cavity of the external body, wherein the cover defining an expandable opening, wherein cover is configured to allow the pair of jaws to enter the internal cavity via the expandable opening to grasp the applicator pad.

17. The apparatus of claim 16, wherein the cover comprises a seal, wherein the seal defines the expandable opening.

* * * * *